US010717949B2

(12) United States Patent
Yamada et al.

(10) Patent No.: US 10,717,949 B2
(45) Date of Patent: Jul. 21, 2020

(54) ALKALINE PROTEASE VARIANT

(71) Applicant: Kao Corporation, Chuo-ku, Tokyo (JP)

(72) Inventors: Kozo Yamada, Wakayama (JP); Tsuyoshi Sato, Tokyo (JP)

(73) Assignee: Kao Corporation, Tokyo (JP)

(*) Notice: Subject to any disclaimer, the term of this patent is extended or adjusted under 35 U.S.C. 154(b) by 49 days.

(21) Appl. No.: 16/307,634

(22) PCT Filed: Jun. 7, 2017

(86) PCT No.: PCT/JP2017/021079
§ 371 (c)(1),
(2) Date: Dec. 6, 2018

(87) PCT Pub. No.: WO2017/213168
PCT Pub. Date: Dec. 14, 2017

(65) Prior Publication Data
US 2019/0161708 A1    May 30, 2019

(30) Foreign Application Priority Data

Jun. 9, 2016 (JP) .................................. 2016-115734
May 25, 2017 (JP) .................................. 2017-103390

(51) Int. Cl.
C12N 9/54        (2006.01)
C12N 15/75       (2006.01)
(Continued)

(52) U.S. Cl.
CPC .......... C11D 3/38636 (2013.01); C11D 3/386 (2013.01); C12N 1/16 (2013.01); C12N 1/20 (2013.01); C12N 9/54 (2013.01); C12N 15/09 (2013.01); C12N 15/75 (2013.01); C12Y 304/2404 (2013.01)

(58) Field of Classification Search
None
See application file for complete search history.

(56) References Cited

U.S. PATENT DOCUMENTS

2004/0002432 A1    1/2004  Okuda et al.
2004/0142837 A1    7/2004  Takaiwa et al.
(Continued)

FOREIGN PATENT DOCUMENTS

CN    101627119 A    1/2010
CN    104204201 A    12/2014
(Continued)

OTHER PUBLICATIONS

UniProt Accession No. Q9AQR0_9BACI, published Jun 1, 2001 (Year: 2001).*

(Continued)

Primary Examiner — Richard C Ekstrom
(74) Attorney, Agent, or Firm — Sterne, Kessler, Goldstein & Fox P.L.L.C.

(57) ABSTRACT

Provided is an alkaline protease mutant with improved stability to a chelating agent. An alkaline protease mutant, in which an amino acid residue at a position corresponding to position 294 of the amino acid sequence as shown in SEQ ID NO: 2 is substituted in the amino acid sequence as shown in SEQ ID NO: 2, or an amino acid sequence having an identity of at least 95% thereto.

20 Claims, 3 Drawing Sheets

Specification includes a Sequence Listing.

(51) Int. Cl.
  *C12N 1/16* (2006.01)
  *C12N 1/20* (2006.01)
  *C11D 3/386* (2006.01)
  *C12N 15/09* (2006.01)

(56) References Cited

U.S. PATENT DOCUMENTS

| | | |
|---|---|---|
| 2008/0177040 A1 | 7/2008 | Okuda et al. |
| 2010/0184188 A1 | 7/2010 | Okuda |
| 2015/0056681 A1 | 2/2015 | Tohata et al. |
| 2019/0161708 A1* | 5/2019 | Yamada .................. C12N 5/10 |

FOREIGN PATENT DOCUMENTS

| | | |
|---|---|---|
| JP | 2003-125783 A | 5/2003 |
| JP | 2004-000122 A | 1/2004 |
| JP | 2004-008085 A | 1/2004 |
| JP | 2004-057195 A | 2/2004 |
| JP | 2004-187699 A | 7/2004 |
| JP | 2004-305175 A | 11/2004 |
| JP | 2004-305176 A | 11/2004 |
| JP | 2008-022828 A | 2/2008 |
| JP | 2010-273673 A | 12/2010 |
| JP | 2011-200249 A | 10/2011 |
| WO | WO 99/018218 A1 | 4/1999 |
| WO | WO 2006/032278 A1 | 3/2006 |
| WO | WO 2010/126156 A2 | 11/2010 |

OTHER PUBLICATIONS

International Search Report (ISR) for PCT/JP2017/021079; I.A. fd Jun. 7, 2017, dated Aug. 29, 2017, from the Japan Patent Office, Tokyo, Japan.

International Preliminary Report on Patentability (IPRP), Chapter I of the Patent Cooperation Treaty, including the Written Opinion for PCT/JP2017/021079; I.A. fd Jun. 7, 2017, dated Dec. 11, 2018, by the International Bureau of WIPO, Geneva, Switzerland.

The partial supplementary European search report including the provisional opinion accompanying the partial search result, for EP Application No. 17810342.0, dated Dec. 13, 2019, European Patent Office, Munich, Germany.

* cited by examiner

[Figure 1]
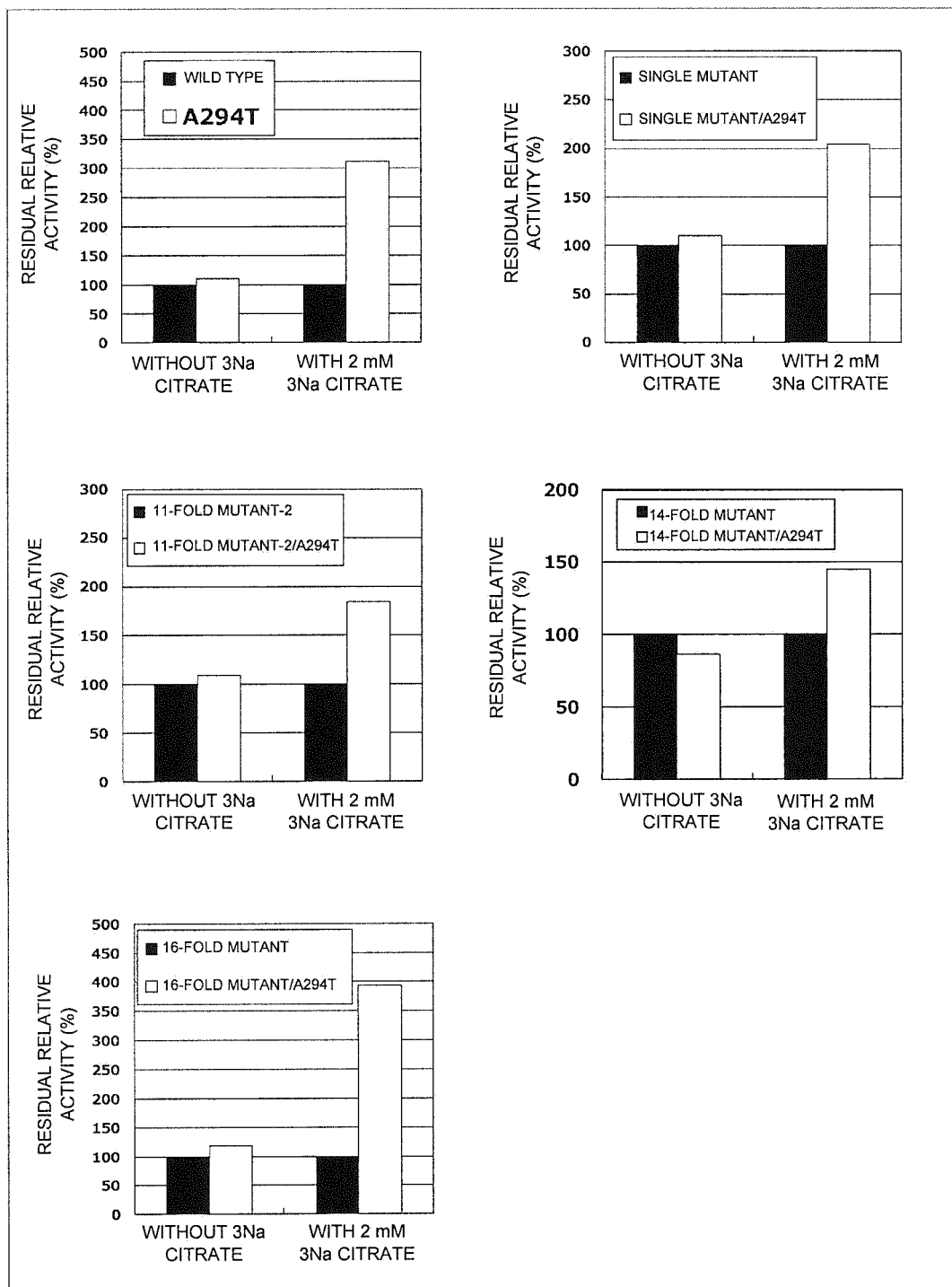

[Figure 2]
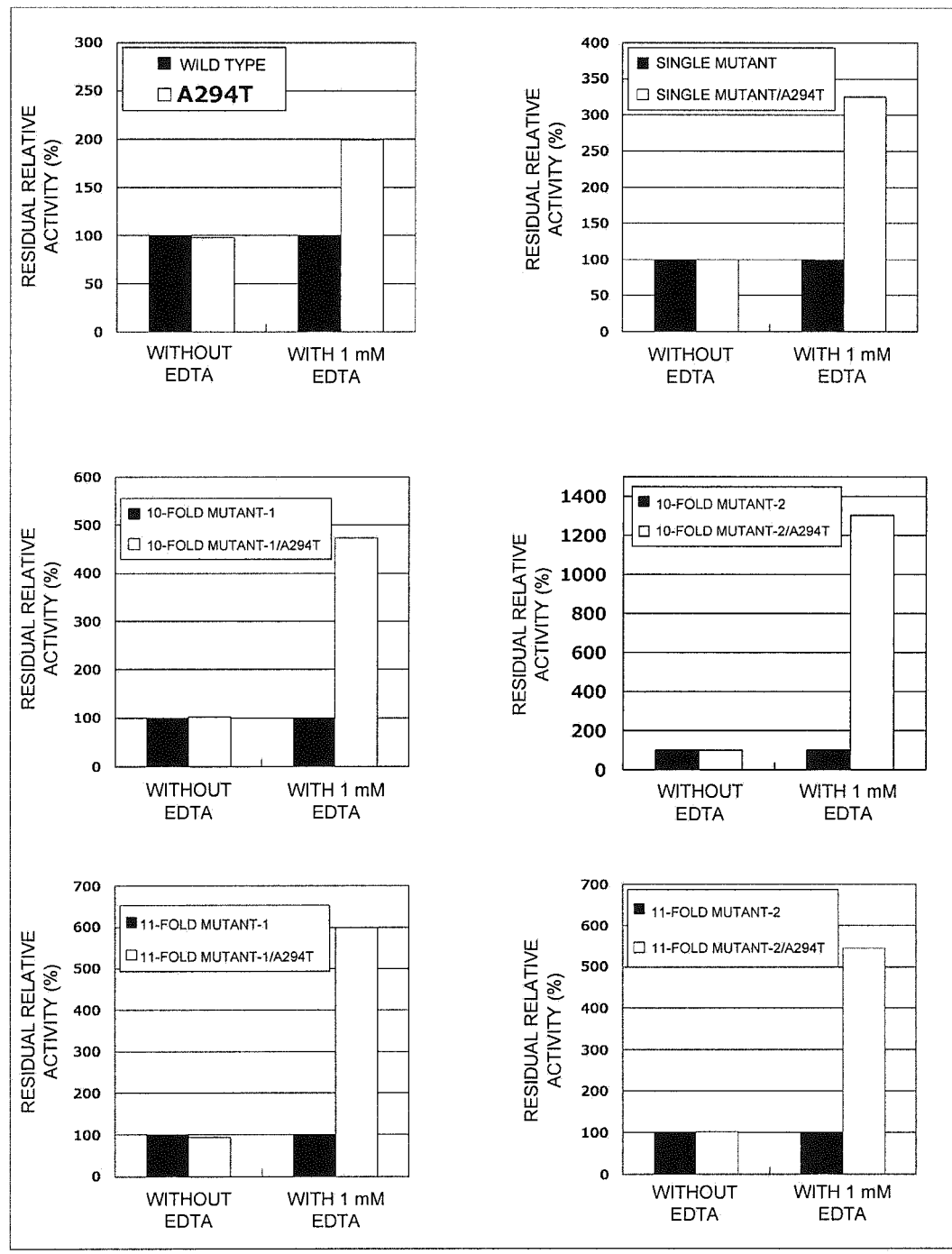

[Figure 3]
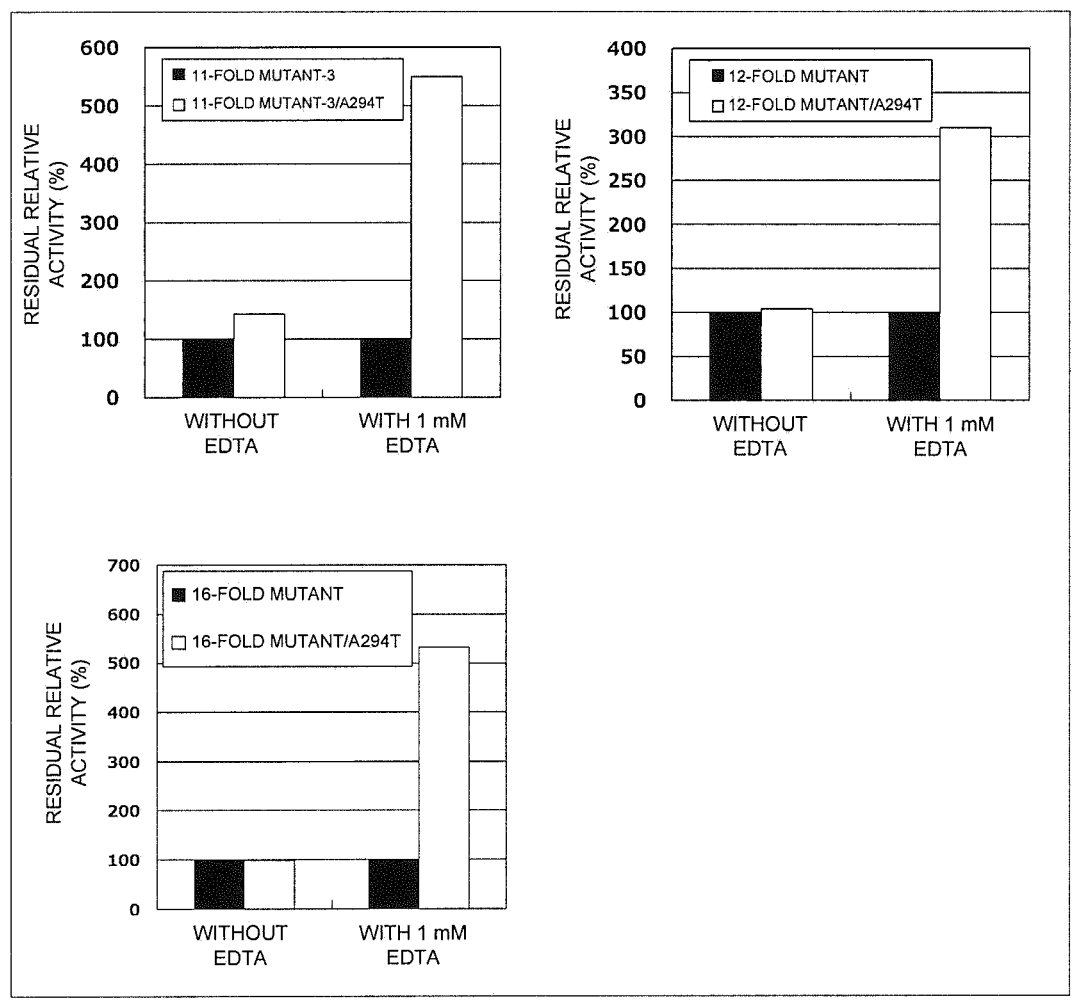

SEQUENCE LISTING

<160> NUMBER OF SEQ ID NOS: 13

<210> SEQ ID NO 1
<211> LENGTH: 1302
<212> TYPE: DNA
<213> ORGANISM: Bacillus sp. KSM-KP43

```
<220> FEATURE:
<223> OTHER INFORMATION: Wild-type

<400> SEQUENCE: 1
aatgatgttg cgcgtggaat tgtcaaagcg gatgtggctc agagcagcta cgggttgtat      60
ggacaaggac agatcgtagc ggttgccgat acagggcttg atacaggtcg caatgacagt     120
tcgatgcatg aagccttccg cggaaaaatt actgcattat atgcattggg acggacgaat     180
aatgccaatg atacgaatgg tcatggtacg catgtggctg gctccgtatt aggaaacggc     240
tccactaata aaggaatggc gcctcaggcg aatctagtct tccaatctat catggatagc     300
ggtgggggac ttggaggact accttcgaat ctgcaaacct tattcagcca agcatacagt     360
gctggtgcca gaattcatac aaactcctgg ggagcagcag tgaatggggc ttacacaaca     420
gattccagaa atgtggatga ctatgtgcgc aaaaatgata tgacgatcct tttcgctgcc     480
gggaatgaag gaccgaacgg cggaaccatc agtgcaccag gcacagctaa aaatgcaata     540
acagtcggag ctacggaaaa cctccgccca agctttgggt cttatgcgga caatatcaac     600
catgtggcac agttctcttc acgtggaccg acaaaggatg gacggatcaa accggatgtc     660
atggcaccgg gaacgttcat actatcagca agatcttctc ttgcaccgga ttcctccttc     720
tgggcgaacc atgacagtaa atatgcatac atgggtggaa cgtccatggc tacaccgatc     780
gttgctggaa acgtggcaca gcttcgtgag cattttgtga aaaacagagg catcacacca     840
aagccttctc tattaaaagc ggcactgatt gccggtgcag ctgacatcgg ccttggctac     900
ccgaacggta accaaggatg gggacgagtg acattggata atccctgaa cgttgcctat      960
gtgaacgagt ccagttctct atccaccagc caaaaagcga cgtactcgtt tactgctact    1020
gccggcaagc ctttgaaaat ctccctggta tggtctgatg cccctgcgag cacaactgct    1080
tccgtaacgc ttgtcaatga tctggaccct gtcattaccg ctccaaatgg cacacagtat    1140
gtaggaaatg actttacttc gccatacaat gataactggg atggccgcaa taacgtagaa    1200
aatgtatttta ttaatgcacc acaaagcggg acgtatacaa ttgaggtaca ggcttataac    1260
gtaccggttg gaccacagac cttctcgttg gcaattgtga at                        1302
```

```
<210> SEQ ID NO 2
<211> LENGTH: 434
<212> TYPE: PRT
<213> ORGANISM: Bacillus sp. KSM-KP43
<220> FEATURE:
<223> OTHER INFORMATION: Wild-type

<400> SEQUENCE: 2

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110
```

```
Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
        130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Gln Tyr Val Gly Asn Asp
    370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 3
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 3

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30
```

```
Leu Asp Thr Gly Arg Asn Asp Ser Met His Glu Ala Phe Arg Gly
         35                  40                  45

Lys Ile Thr Ala Leu Tyr Ala Leu Gly Arg Thr Asn Asn Ala Asn Asp
 50                  55                  60

Thr Asn Gly His Gly Thr His Val Ala Gly Ser Val Leu Gly Asn Gly
 65                  70                  75                  80

Ser Thr Asn Lys Gly Met Ala Pro Gln Ala Asn Leu Val Phe Gln Ser
                 85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
            115                 120                 125

Ser Trp Gly Thr Ala Val Asn Gly Ala Tyr Thr Thr Asp Ser Arg Asn
            130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
            210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
            275                 280                 285

Leu Ile Ala Gly Ala Ala Asp Ile Gly Leu Gly Tyr Pro Asn Gly Asn
            290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
            355                 360                 365

Asp Leu Val Ile Thr Ala Pro Asn Gly Thr Gln Tyr Val Gly Asn Asp
            370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 4
```

<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 4

```
Asn Asp Val Ala Arg Gly Ile Val Lys Ala Asp Val Ala Gln Ser Val
1               5                  10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Gly
65                  70                  75                  80

Ser Thr Ala Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Gln Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Ser Ala Ser Val Thr Leu Val Asn Asp Leu
        355                 360                 365

Asn Leu Val Ile Thr Ala Pro Asn Gly Thr Gln Tyr Val Gly Asn Asp
    370                 375                 380
```

```
Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
            405                 410                 415

Gln Ala Tyr Asn Val Pro Val Gly Pro Gln Thr Phe Ser Leu Ala Ile
        420                 425                 430

Val Asn

<210> SEQ ID NO 5
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 5

Asn Asp Val Ala Arg Gly Ile Val Lys Ala Asp Val Ala Gln Ser Val
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
50                  55                  60

Pro Asn Gly His Gly Thr His Val Ala Gly Ser Val Leu Gly Asn Gly
65                  70                  75                  80

Ser Thr Ala Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Thr Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Gln Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
290                 295                 300
```

-continued

```
Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
            325                 330                 335

Phe Thr Ala Thr Ala Gly Lys Pro Leu Lys Ile Ser Leu Val Trp Ser
                340                 345                 350

Asp Ala Pro Ala Ser Thr Ser Ala Ser Val Thr Leu Val Asn Asp Leu
            355                 360                 365

Asn Leu Val Ile Thr Ala Pro Asn Gly Thr Gln Tyr Val Gly Asn Asp
        370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 6
<211> LENGTH: 435
<212> TYPE: PRT
<213> ORGANISM: Bacillus sp. KSM-KP43
<220> FEATURE:
<223> OTHER INFORMATION: Valiant

<400> SEQUENCE: 6

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ser Ser Thr Asn Gly Ala Tyr Thr Thr Asp Ser Arg
    130                 135                 140

Asn Val Asp Asp Tyr Val Arg Lys Asn Asp Met Thr Ile Leu Phe Ala
145                 150                 155                 160

Ala Gly Asn Glu Gly Pro Gly Val Gly Thr Ile Ser Ala Pro Gly Thr
                165                 170                 175

Ala Lys Asn Ala Ile Thr Val Gly Ala Thr Glu Asn Leu Arg Pro Ser
            180                 185                 190

Phe Gly Ser Gln Ala Asp Asn Ile Asn His Val Ala Gln Phe Ser Ser
        195                 200                 205

Arg Gly Pro Thr Lys Asp Gly Arg Ile Lys Pro Asp Val Met Ala Pro
    210                 215                 220

Gly Thr Phe Ile Leu Ser Ala Arg Ser Ser Leu Ala Pro Asp Ser Ser
```

-continued

```
            225                 230                 235                 240
        Phe Trp Ala Asn His Asp Ser Lys Tyr Ala Tyr Met Gly Gly Thr Ser
                            245                 250                 255

Met Ala Thr Pro Ile Val Ala Gly Asn Val Ala Gln Leu Arg Glu His
                    260                 265                 270

Phe Ile Lys Asn Arg Gly Ile Thr Pro Lys Pro Ser Leu Leu Lys Ala
                275                 280                 285

Ala Leu Ile Ala Gly Ala Ala Asp Ile Gly Leu Gly Tyr Pro Asn Gly
            290                 295                 300

Asn Gln Gly Trp Gly Arg Val Thr Leu Asp Lys Ser Leu Asn Val Ala
        305                 310                 315                 320

Tyr Val Asn Glu Ser Ser Leu Ser Thr Ser Gln Lys Ala Thr Tyr
                        325                 330                 335

Ser Phe Thr Ala Thr Ala Gly Lys Pro Leu Lys Ile Ser Leu Val Trp
                    340                 345                 350

Ser Asp Ala Pro Ala Ser Thr Ser Ala Ser Val Thr Leu Val Asn Asp
                355                 360                 365

Leu Asn Leu Val Ile Thr Ala Pro Asn Gly Thr Gln Tyr Val Gly Asn
            370                 375                 380

Asp Phe Thr Ala Pro Tyr Asn Asp Asn Trp Asp Gly Arg Asn Asn Val
        385                 390                 395                 400

Glu Asn Val Phe Ile Asn Ala Pro Gln Ser Gly Thr Tyr Thr Ile Glu
                        405                 410                 415

Val Gln Ala Tyr Asn Val Pro Val Gly Pro Gln Thr Phe Ser Leu Ala
                    420                 425                 430

Ile Val Asn
                435

<210> SEQ ID NO 7
<211> LENGTH: 435
<212> TYPE: PRT
<213> ORGANISM: Bacillus sp. KSM-KP43
<220> FEATURE:
<223> OTHER INFORMATION: Valiant

<400> SEQUENCE: 7

Asn Asp Val Ala Arg Gly Ile Val Lys Ala Asp Val Ala Gln Ser Ser
        1               5                   10                  15

Tyr Gly Leu Tyr Gly Gln Gly Gln Ile Val Ala Val Ala Asp Thr Gly
                    20                  25                  30

Leu Asp Thr Gly Arg Asn Asp Ile Ser Met His Glu Ala Phe Arg Gly
                35                  40                  45

Lys Ile Thr Ala Leu Tyr Ala Leu Gly Arg Val Asn Asn Ala Asn Asp
            50                  55                  60

Pro Asn Gly His Gly Thr His Val Ala Gly Ser Val Leu Gly Asn Gly
        65                  70                  75                  80

Leu Thr Asn Lys Gly Met Ala Pro Gln Ala Asn Leu Val Phe Gln Ser
                        85                  90                  95

Ile Met Asp Ser Gly Gly Gly Leu Gly Gly Leu Pro Ser Asn Leu Gln
                    100                 105                 110

Thr Leu Phe Ser Gln Ala Tyr Ser Ala Gly Ala Arg Ile His Thr Asn
                115                 120                 125

Ser Trp Gly Ala Ser Ser Thr Asn Gly Ala Tyr Thr Thr Asp Ser Arg
            130                 135                 140

Asn Val Asp Asp Tyr Val Arg Lys Asn Asp Met Thr Ile Leu Phe Ala
```

```
            145                 150                 155                 160
        Ala Gly Asn Glu Gly Pro Gly Val Gly Thr Ile Ser Ala Pro Gly Thr
                        165                 170                 175

Ala Lys Asn Ala Ile Thr Val Gly Ala Thr Glu Asn Leu Arg Pro Leu
                        180                 185                 190

Phe Gly Ser Gln Ala Asp Asn Ile Asn His Val Ala Gln Phe Ser Ser
                        195                 200                 205

Arg Gly Pro Thr Lys Asp Gly Arg Ile Lys Pro Asp Val Met Ala Pro
                        210                 215                 220

Gly Thr Phe Ile Leu Ser Ala Arg Ser Ser Leu Ala Pro Asp Ser Ser
        225                 230                 235                 240

Phe Trp Ala Asn His Asp Ser Lys Tyr Ala Tyr Met Gly Gly Thr Ser
                        245                 250                 255

Met Ala Thr Pro Ile Val Ala Gly Asn Val Ala Gln Leu Arg Glu His
                        260                 265                 270

Phe Ile Lys Asn Arg Gly Ile Thr Pro Lys Pro Ser Leu Leu Lys Ala
                        275                 280                 285

Ala Leu Ile Ala Gly Ala Ala Asp Ile Gly Leu Gly Tyr Pro Asn Gly
                        290                 295                 300

Asn Gln Gly Trp Gly Arg Val Thr Leu Asp Lys Ser Leu Asn Val Ala
        305                 310                 315                 320

Tyr Val Asn Glu Ser Ser Leu Ser Thr Ser Gln Lys Ala Thr Tyr
                        325                 330                 335

Ser Phe Thr Ala Thr Ala Gly Lys Pro Leu Lys Ile Ser Leu Val Trp
                        340                 345                 350

Ser Asp Ala Pro Ala Ser Thr Ser Ala Ser Val Thr Leu Val Asn Asp
                        355                 360                 365

Leu Asn Leu Val Ile Thr Ala Pro Asn Gly Thr Gln Tyr Val Gly Asn
                        370                 375                 380

Asp Phe Thr Ala Pro Tyr Asn Asp Asn Trp Asp Gly Arg Asn Asn Val
        385                 390                 395                 400

Glu Asn Val Phe Ile Leu Ala Pro Gln Ser Gly Thr Tyr Thr Ile Glu
                        405                 410                 415

Val Gln Ala Tyr Asn Val Pro Val Gly Pro Gln Thr Phe Ser Leu Ala
                        420                 425                 430

Ile Val Asn
                435

<210> SEQ ID NO 8
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 8

Asn Asp Val Ala Arg Gly Ile Val Lys Ala Asp Val Ala Gln Ser Ser
        1               5                   10                  15

Tyr Gly Leu Tyr Gly Gln Gly Gln Ile Val Ala Val Ala Asp Thr Gly
                        20                  25                  30

Leu Asp Thr Gly Arg Asn Asp Ser Ser Met His Glu Ala Phe Arg Gly
                        35                  40                  45

Lys Ile Thr Ala Leu Tyr Ala Leu Gly Arg Thr Asn Asn Ala Asn Asp
                        50                  55                  60

Pro Asn Gly His Gly Thr His Val Ala Gly Ser Val Leu Gly Asn Gly
```

65                  70                  75                  80
Ser Thr Ala Lys Gly Met Ala Pro Gln Ala Asn Leu Val Phe Gln Ser
                    85                  90                  95

Ile Met Asp Ser Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
                115                 120                 125

Ser Trp Gly Thr Ala Val Asn Gly Ala Tyr Thr Thr Asp Ser Arg Asn
            130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
                180                 185                 190

Gly Ser Arg Ala Asp Asn Ile Asn His Val Ala Gln Phe Ser Ser Arg
            195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
                260                 265                 270

Ile Lys Asn Arg Gly Ile Thr Pro Lys Pro Ser Leu Leu Lys Ala Ala
            275                 280                 285

Leu Ile Ala Gly Ala Ala Asp Ile Gly Leu Gly Tyr Pro Asn Gly Asn
        290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
                340                 345                 350

Asp Ala Pro Ala Ser Thr Ser Ala Ser Val Thr Leu Val Asn Asp Leu
            355                 360                 365

Asn Leu Val Ile Thr Ala Pro Asn Gly Thr Gln Tyr Val Gly Asn Asp
        370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
                420                 425                 430

Val Asn

<210> SEQ ID NO 9
<211> LENGTH: 435
<212> TYPE: PRT
<213> ORGANISM: Bacillus sp. KSM-KP43
<220> FEATURE:
<223> OTHER INFORMATION: Valiant

<400> SEQUENCE: 9

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Gly
65              70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ser Ser Thr Asn Gly Ala Tyr Thr Thr Asp Ser Arg
    130                 135                 140

Asn Val Asp Asp Tyr Val Arg Lys Asn Asp Met Thr Ile Leu Phe Ala
145                 150                 155                 160

Ala Gly Asn Glu Gly Pro Gly Val Gly Thr Ile Ser Ala Pro Gly Thr
                165                 170                 175

Ala Lys Asn Ala Ile Thr Val Gly Ala Thr Glu Asn Leu Arg Pro Ser
            180                 185                 190

Phe Gly Ser Arg Ala Asp Asn Ile Asn His Val Ala Gln Phe Ser Ser
            195                 200                 205

Arg Gly Pro Thr Lys Asp Gly Arg Ile Lys Pro Asp Val Met Ala Pro
    210                 215                 220

Gly Thr Phe Ile Leu Ser Ala Arg Ser Ser Leu Ala Pro Asp Ser Ser
225                 230                 235                 240

Phe Trp Ala Asn His Asp Ser Lys Tyr Ala Tyr Met Gly Gly Thr Ser
                245                 250                 255

Met Ala Thr Pro Ile Val Ala Gly Asn Val Ala Gln Leu Arg Glu His
                260                 265                 270

Phe Ile Lys Asn Arg Gly Ile Thr Pro Lys Pro Ser Leu Leu Lys Ala
            275                 280                 285

Ala Leu Ile Ala Gly Ala Ala Asp Ile Gly Leu Gly Tyr Pro Asn Gly
            290                 295                 300

Asn Gln Gly Trp Gly Arg Val Thr Leu Asp Lys Ser Leu Asn Val Ala
305                 310                 315                 320

Tyr Val Asn Glu Ser Ser Ser Leu Ser Thr Ser Gln Lys Ala Thr Tyr
                325                 330                 335

Ser Phe Thr Ala Thr Ala Gly Lys Pro Leu Lys Ile Ser Leu Val Trp
            340                 345                 350

Ser Asp Ala Pro Ala Ser Thr Ser Ala Ser Val Thr Leu Val Asn Asp
            355                 360                 365

Leu Asn Leu Val Ile Thr Ala Pro Asn Gly Thr Gln Tyr Val Gly Asn
            370                 375                 380

Asp Phe Thr Ala Pro Tyr Asn Asp Asn Trp Asp Gly Arg Asn Asn Val
385                 390                 395                 400

Glu Asn Val Phe Ile Asn Ala Pro Gln Ser Gly Thr Tyr Thr Ile Glu
                405                 410                 415
```

Val Gln Ala Tyr Asn Val Pro Val Gly Pro Gln Thr Phe Ser Leu Ala
                420                 425                 430

Ile Val Asn
        435

<210> SEQ ID NO 10
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 10

Asn Asp Val Ala Arg Gly Ile Val Lys Ala Asp Val Ala Gln Ser Val
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
50                  55                  60

Pro Asn Gly His Gly Thr His Val Ala Gly Ser Val Leu Gly Asn Gly
65                  70                  75                  80

Ser Thr Ala Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Gln Ala Asp Asn Ile Asn His Val Ala Asp Phe Ser Ser Arg
            195                 200                 205

Gly Pro Thr Lys Asp Gly Arg Ile Lys Pro Asp Val Met Ala Pro Gly
210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
            275                 280                 285

Leu Ile Ala Gly Ala Ala Asp Ile Gly Leu Gly Tyr Pro Asn Gly Asn
290                 295                 300

Gln Gly Trp Gly Arg Val Thr Leu Asp Lys Ser Leu Asn Val Val Tyr
305                 310                 315                 320

Val Asn Glu Ser Ser Ser Leu Ser Thr Ser Gln Lys Ala Thr Tyr Ser
                325                 330                 335

```
Phe Thr Ala Thr Ala Gly Lys Pro Leu Lys Ile Ser Leu Val Trp Ser
                340                 345                 350

Asp Ala Pro Ala Ser Thr Ser Ala Ser Val Thr Leu Val Asn Asp Leu
            355                 360                 365

Asn Leu Val Ile Thr Ala Pro Asn Gly Thr Gln Tyr Val Gly Asn Asp
        370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 11
<211> LENGTH: 435
<212> TYPE: PRT
<213> ORGANISM: Bacillus sp. KSM-KP43
<220> FEATURE:
<223> OTHER INFORMATION: Valiant

<400> SEQUENCE: 11

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
        50                  55                  60

Pro Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ser Ser Thr Asn Gly Ala Tyr Thr Thr Asp Ser Arg
        130                 135                 140

Asn Val Asp Asp Tyr Val Arg Lys Asn Asp Met Thr Ile Leu Phe Ala
145                 150                 155                 160

Ala Gly Asn Glu Gly Pro Gly Val Gly Thr Ile Ser Ala Pro Gly Thr
                165                 170                 175

Ala Lys Asn Ala Ile Thr Val Gly Ala Thr Glu Asn Leu Arg Pro Ser
            180                 185                 190

Phe Gly Arg Arg Ala Asp Asn Ile Asn His Val Ala Gln Phe Ser Ser
        195                 200                 205

Arg Gly Pro Thr Arg Asp Gly Arg Ile Lys Pro Asp Val Met Ala Pro
210                 215                 220

Gly Thr Phe Ile Leu Ser Ala Arg Ser Ser Leu Ala Pro Asp Ser Ser
225                 230                 235                 240

Phe Trp Ala Asn His Asp Ser Lys Tyr Ala Tyr Met Gly Gly Thr Ser
                245                 250                 255

Met Ala Thr Pro Ile Val Ala Gly Asn Val Ala Gln Leu Arg Glu His
```

```
                     260                 265                 270
Phe Ile Lys Asn Arg Gly Ile Thr Pro Lys Pro Ser Leu Leu Lys Ala
                275                 280                 285

Ala Leu Ile Ala Gly Ala Ala Asp Ile Gly Leu Gly Tyr Pro Asn Gly
                290                 295                 300

Asn Gln Gly Trp Gly Arg Val Thr Leu Asp Lys Ser Leu Asn Val Ala
305                 310                 315                 320

Tyr Val Asn Glu Ser Ser Ser Leu Ser Thr Ser Gln Lys Ala Thr Tyr
                325                 330                 335

Ser Phe Thr Ala Thr Ala Gly Lys Pro Leu Lys Ile Ser Leu Val Trp
                340                 345                 350

Ser Asp Ala Pro Ala Ser Thr Ser Ala Ser Val Thr Leu Val Asn Asp
                355                 360                 365

Leu Asn Leu Val Ile Thr Ala Pro Asn Gly Thr Arg Tyr Val Gly Asn
                370                 375                 380

Asp Phe Thr Ala Pro Tyr Asn Asp Asn Trp Asp Gly Arg Asn Asn Val
385                 390                 395                 400

Glu Asn Val Phe Ile Asn Ala Pro Gln Ser Gly Thr Tyr Thr Ile Glu
                405                 410                 415

Val Gln Ala Tyr Asn Val Pro Val Gly Pro Gln Thr Phe Ser Leu Ala
                420                 425                 430

Ile Val Asn
        435

<210> SEQ ID NO 12
<211> LENGTH: 27
<212> TYPE: DNA
<213> ORGANISM: Artificial
<220> FEATURE:
<223> OTHER INFORMATION: Oligonucleotide primer A294-F

<400> SEQUENCE: 12
ggtgcaactg acatcggcct tggctac                                    27

<210> SEQ ID NO 13
<211> LENGTH: 27
<212> TYPE: DNA
<213> ORGANISM: Artificial
<220> FEATURE:
<223> OTHER INFORMATION: Oligonucleotide primer A294-R

<400> SEQUENCE: 13
gatgtcagtt gcaccggcaa tcagtgc                                    27
```

ALKALINE PROTEASE VARIANT

FIELD OF THE INVENTION

The present invention relates to an alkaline protease mutant.

BACKGROUND OF THE INVENTION

Detergent can be classified into a powder detergent and a liquid detergent, based on the form thereof. A liquid detergent is excellent in terms of solubility, in comparison to a powder detergent. Also, the liquid detergent is advantageous in that an undiluted detergent can be directly applied to stains. On the other hand, in the case of such a liquid detergent, since an enzyme such as a protease must be preserved at ordinary temperature in the liquid, it has technical difficulty in terms of stable preservation of the enzyme, differing from a powder detergent.

Moreover, since a liquid detergent contains a surfactant, fatty acid, a solvent, a chelating agent and the like, it imposes extremely strict conditions on the enzyme. For example, it has been conventionally known to add calcium ions as a means for stabilizing the enzyme in a liquid detergent. However, since a chelating agent comprised in such a liquid detergent has a property of taking calcium ions coordinated to the enzyme, it reduces an effect of stabilizing calcium ions and thereby destabilizes the enzyme.

An object of mixing a protease into a detergent is to decompose protein stains on clothes into low molecules, and thus, to promote removal of the stains. As a detergent protease, an alkaline protease with a molecular weight of approximately 43,000, which has a washing performance on composite stains containing lipids as well as proteins, has been developed so far (see Patent Literature 1). Moreover, studies have been conducted to cause alkaline protease to mutate, so as to improve specific activity, or stability, etc., thereby enhancing the washing performance thereof (Patent Literatures 2 and 3).
(Patent Literature 1) WO 99/18218
(Patent Literature 2) JP-A-2010-273673
(Patent Literature 3) JP-B-5202690

SUMMARY OF THE INVENTION

In one aspect, the present invention provides an alkaline protease mutant consisting of an amino acid sequence obtained by substituting an amino acid residue at a position corresponding to position 294 in the amino acid sequence as shown in SEQ ID NO:2 with threonine in the amino acid sequence as shown in SEQ ID NO:2 or an amino acid sequence having an identity of at least 95% thereto.

In another aspect, the present invention provides a polynucleotide encoding the above described alkaline protease mutant.

In another aspect, the present invention provides a vector comprising the above described polynucleotide.

In another aspect, the present invention provides a transformant comprising the above described polynucleotide or the above described vector.

In another aspect, the present invention provides a method for producing an alkaline protease mutant, using the above described transformant.

In a further aspect, the present invention provides a detergent composition comprising the above described alkaline protease mutant.

In a further aspect, the present invention provides a method for producing an alkaline protease mutant, comprising substituting the amino acid residue at a position corresponding to position 294 of the amino acid sequence as shown in SEQ ID NO: 2 with threonine, in the amino acid sequence as shown in SEQ ID NO: 2, or an amino acid sequence having an identity of at least 95% thereto.

In a further aspect, the present invention provides a method for improving stability of alkaline protease to a chelating agent, comprising substituting the amino acid residue at a position corresponding to position 294 of the amino acid sequence as shown in SEQ ID NO: 2 with threonine, in the amino acid sequence as shown in SEQ ID NO: 2, or an amino acid sequence having an identity of at least 95% thereto.

BRIEF DESCRIPTION OF THE DRAWINGS

FIG. 1 shows the relative residual activity of an alkaline protease mutant in a citrate aqueous solution.

FIG. 2 shows the relative residual activity of an alkaline protease mutant in an EDTA aqueous solution.

FIG. 3 shows the relative residual activity of an alkaline protease mutant in an EDTA aqueous solution.

DETAILED DESCRIPTION OF THE INVENTION

In the present description, the term "amino acid residue" refers to 20 types of amino acid residues constituting a protein, namely, alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

In the present description, an identity between nucleotide sequences or between amino acid sequences can be calculated according to a Lipman-Pearson method (Science, 1985, 227: 1435-41). Specifically, by employing the homology analysis (Search homology) program of the gene information processing software Genetyx-Win (Ver. 5.1.1; Software Development), such an identity can be calculated by performing an analysis, setting Unit size to compare (ktup) at 2.

In the present description, the "amino acid sequence in which one or more amino acids are deleted, inserted, substituted or added" may be an amino acid sequence in which 1 or more and 20 or less, preferably 1 or more and 10 or less, more preferably 1 or more and 5 or less, further preferably 1 or more and 3 or less amino acids are deleted, inserted, substituted or added. In addition, in the present description, the "nucleotide sequence in which one or more nucleotides are deleted, inserted, substituted or added" may be a nucleotide sequence in which 1 or more and 60 or less, preferably 1 or more and 30 or less, more preferably 1 or more and 15 or less, further preferably 1 or more and 10 or less nucleotides are deleted, inserted, substituted or added. Moreover, in the present description, "addition" of amino acids or nucleotides includes addition of one or more amino acids or nucleotides to one terminus or both termini of the sequence.

In the present description, the "corresponding position" on an amino acid sequence or a nucleotide sequence can be determined by aligning a target sequence and a reference sequence (e.g., the amino acid sequence as shown in SEQ ID NO: 2) such that they give the maximum homology to conserved amino acid residues or nucleotides present in each amino acid sequence or nucleotide sequence. Such alignment can be carried out using a known algorithm, and the procedures thereof are known to a person skilled in the art. For example, the alignment can be manually carried out based on the aforementioned Lipman-Pearson method, etc. Also, the alignment can be carried out using Clustal W Multiple Alignment Program (Thompson, J. D. et al, 1994, Nucleic Acids Res, 22: 4673-4680) with default setting. Otherwise, Clustal W2 or Clustal omega, which is a revision of Clustal W, can also be used. Such Clustal W, Clustal W2, and Clustal omega are available, for example, on the website of European Bioinformatics Institute (EBI [www.ebi.ac.uk/index.html]), or the website of DNA Data Bank of Japan (DDBJ [www.ddbj.nig.ac.jp/Welcome-j.html]) handled by National Institute of Genetics.

A person skilled in the art can further finely adjust the above obtained alignment of amino acid sequences, so that it can be optimized. Such optimal alignment is preferably determined, while taking into consideration the similarity of amino acid sequences, the frequency of inserted gaps, etc. In this context, the similarity of amino acid sequences means the ratio (%) of the number of the positions, at which identical or analogous amino acid residues are present in two amino acid sequences, relative to the number of full-length amino acid residues, when the two amino acid sequences are aligned to each other. Analogous amino acid residues mean amino acid residues, which have similar properties to each other in polarity and electric charge and cause, what is called, conservative substitution, among 20 types of amino acids constituting a protein. Groups consisting of such analogous amino acid residues are well known to a person skilled in the art, and examples of such groups include: arginine and lysine or glutamine; glutamic acid and aspartic acid or glutamine; serine and threonine or alanine; glutamine and asparagine or arginine; and leucine and isoleucine, but the examples are not limited thereto.

The position of the amino acid residue of a target amino acid sequence, which is aligned to a position corresponding to an arbitrary position of the reference sequence according to the aforementioned alignment, is considered to be the "position corresponding to" the arbitrary position, and the amino acid residue is referred to as the "amino acid residue at a corresponding position."

In the present description, the "parent" polynucleotide or polypeptide of a given mutant polynucleotide or polypeptide means a polynucleotide or polypeptide, which is converted to the mutant polynucleotide or polypeptide by introducing a certain mutation into the nucleotide or amino acid residue thereof.

In addition, in the present description, the "operable linking" of a regulatory region to a gene means that the gene is linked to the regulatory region such that the gene can be expressed under the control of the regulatory region. The procedures for "operably linking" of the gene to the regulatory region are well known to a person skilled in the art.

In the present description, the terms "upstream" and "downstream" used regarding a gene mean the upstream and downstream of the gene in the transcription direction, unless otherwise specified.

In the present description, the "chelating agent" means a compound capable of coordinate-bonding with metal ions. A chelating agent added to a detergent composition has an action to block metal ions which negatively affect washing of, for example, calcium ions or magnesium ions existing in washing water or stain. Examples of such a chelating agent added to a detergent composition include: aminopolyacetic acids such as nitrilotriacetic acid, iminodiacetic acid, ethylenediamineacetic acid, diethylenetriaminepentaacetic acid, glycol ether diaminetetraacetic acid, hydroxyethyliminodiacetic acid, triethylenetetramine hexaacetic acid, and djenkolic acid, or the salts thereof; organic acids such as diglycolic acid, oxydisuccinic acid, carboxymethyloxysuccinic acid, citric acid, lactic acid, tartaric acid, oxalic acid, malic acid, gluconic acid, carboxymethylsuccinic acid, and carboxymethyltartaric acid, or the salts thereof; aminotri(methylenephosphonic acid), 1-hydroxyethylidene-1,1-diphosphonic acid, ethylenediaminetetra(methylenephosphonic acid), diethylenetriaminepenta(methylenephosphonic acid); and their salts of alkali metals or lower amines.

The present invention relates to provision of an alkaline protease mutant with improved stability to a chelating agent.

The present inventors found that the stability of alkaline protease KP43 having a molecular weight of 43,000 in a liquid containing a chelating agent is improved by substituting the amino acid residue at a specific position in the amino acid sequence thereof with another amino acid residue.

The alkaline protease mutant according to the present invention has high stability to a chelating agent, and thus, is preferable as an enzyme mixed into a composition containing a chelating agent (e.g., a detergent composition). Since a detergent composition containing the alkaline protease mutant according to the present invention is able to stably retain protease activity in a detergent liquid, it can exhibit excellent washing performance to composite stains containing proteins and lipids.

The present invention provides an alkaline protease mutant. The alkaline protease mutant according to the present invention consists of the amino acid sequence as shown in SEQ ID NO:2 or an amino acid sequence having an identity of at least 95% thereto, in which the amino acid residue at a position corresponding to position 294 in the amino acid sequence as shown in SEQ ID NO:2 is substituted.

Examples of a parent alkaline protease of the alkaline protease mutant according to the present invention include an alkaline protease consisting of the amino acid sequence as shown in SEQ ID NO: 2, and an alkaline protease consisting of an amino acid sequence having an identity of at least 95% to the amino acid sequence as shown in SEQ ID NO: 2, in which the amino acid residue at a position corresponding to position 294 is not threonine. The alkaline protease consisting of the amino acid sequence as shown in SEQ ID NO: 2 is, for example, an alkaline protease derived from KP43 [*Bacillus* sp. KSM-KP43 (FERM BP-6532)] (see Patent Literature 1).

One example of the alkaline protease consisting of an amino acid sequence having an identity of at least 95% to the amino acid sequence as shown in SEQ ID NO: 2 is alkaline protease having an identity of 95% or more, preferably 96% or more, more preferably 97% or more, further preferably 98% or more, still further preferably 99% or more, to the amino acid sequence as shown in SEQ ID NO: 2. Another example of the alkaline protease consisting of an amino acid sequence having an identity of at least 95% to the amino acid sequence as shown in SEQ ID NO: 2 is alkaline protease consisting of the amino acid sequence as shown in SEQ ID NO: 2 in which one or more amino acids are deleted, inserted, substituted or added.

Further examples of the alkaline protease consisting of an amino acid sequence having an identity of at least 95% to the amino acid sequence as shown in SEQ ID NO: 2 include protease KP9860 [derived from *Bacillus* sp. KSM-KP9860 (FERM BP-6534); WO99/18218; GenBank Accession No. AB046403] and protease 9865 [derived from *Bacillus* sp. KSM-9865 (FERM P-18566); GenBank Accession No. AB084155].

The alkaline protease consisting of an amino acid sequence having an identity of at least 95% to the amino acid sequence as shown in SEQ ID NO: 2, which is used as a parent alkaline protease in the present invention, may be an alkaline protease mutant derived from the alkaline protease consisting of the amino acid sequence as shown in SEQ ID NO: 2. Examples of the alkaline protease mutant include alkaline protease mutants obtained by introducing one or more of the mutations described in JP-B-5202690, JP-A-2002-218989, JP-A-2002-306176, JP-A-2004-000122, JP-A-2004-305176, JP-A-2006-129865, JP-A-2007-061101, JP-A-2008-212084, JP-A-2009-034062, JP-A-2010-273672, JP-A-2010-273673, JP-A-2012-228216 and JP-A-2013-233141, into the above-described KP-43 strain-derived alkaline protease.

Preferred examples of the aforementioned alkaline protease mutant used as a parent alkaline protease in the present invention include alkaline protease mutants consisting of the amino acid sequence as shown in SEQ ID NO: 2 and having one or more mutations selected from the group consisting of the following (a) to (ds):

(a) substitution of G at position 6 or at a position corresponding thereto with S, T, C, Q, Y, R, K, H, A, V, L, I, M, W or F;

(b) substitution of K at position 9 or at a position corresponding thereto with Q;

(c) substitution of D at position 11 or at a position corresponding thereto with G, S or N;

(d) substitution of S at position 15 or at a position corresponding thereto with H, C, Q, D, E, R, A, V, M, W or F;

(e) substitution of S at position 16 or at a position corresponding thereto with T, Q, V, C, Y, D, E, R, K, H, L, I, M, W or F;

(f) substitution of Y at position 20 or at a position corresponding thereto with F or A;

(g) substitution of Q at position 22 or at a position corresponding thereto with W;

(h) substitution of G at position 23 or at a position corresponding thereto with N;

(i) substitution of R at position 37 or at a position corresponding thereto with T;

(j) substitution of S at position 40 or at a position corresponding thereto with V, L, I, W or F;

(k) substitution of S at position 41 or at a position corresponding thereto with I;

(l) substitution of F at position 46 or at a position corresponding thereto with S, T, C, N, Q, Y, E, K, H, A, V, L, I, M or W;

(m) substitution of K at position 49 or at a position corresponding thereto with Q;

(n) substitution of A at position 52 or at a position corresponding thereto with G or S;

(o) substitution of L at position 53 or at a position corresponding thereto with A, V or I;

(p) substitution of Y at position 54 or at a position corresponding thereto with G, S, T, C, N, Q, D, E, R, H, A, V, M, W, F or P;

(q) substitution of L at position 56 or at a position corresponding thereto with V;

(r) substitution of G at position 57 or at a position corresponding thereto with S, T, C, Q, D, B, R, K, H, A, V, L, I, M, W, F or P;

(s) substitution of T at position 59 or at a position corresponding thereto with V, L, I, M, W or F;

(t) substitution of N at position 60 or at a position corresponding thereto with V, L, I, W or F;

(u) substitution of N at position 63 or at a position corresponding thereto with S, D or L;

(v) substitution of T at position 65 or at a position corresponding thereto with W or P;

(w) substitution of N at position 66 or at a position corresponding thereto with G, S, T, C, Q, D, E, H, A, V, L, I, M or W;

(x) substitution of G at position 80 or at a position corresponding thereto with H or A;

(y) substitution of S at position 81 or at a position corresponding thereto with Q, Y, L, I, W or F;

(z) substitution of T at position 82 or at a position corresponding thereto with G, S, C, Q, D, E, R, K, H, A or M;

(aa) substitution of N at position 83 or at a position corresponding thereto with S, C or A;

(ab) substitution of K at position 84 or at a position corresponding thereto with R;

(ac) substitution of Q at position 89 or at a position corresponding thereto with H;

(ad) substitution of N at position 91 or at a position corresponding thereto with C;

(ae) substitution of S at position 100 or at a position corresponding thereto with L, I, W or F;

(af) substitution of G at position 101 or at a position corresponding thereto with S, T, C, N, Q, Y, D, E, R, K, H, A, V, L, I, M, W, F or P;

(ag) substitution of G at position 102 or at a position corresponding thereto with S, T, C, Q, Y, D, E, R, K, H, A, V, L, I, M, W, F or P;

(ah) substitution of G at position 103 or at a position corresponding thereto with S, T, C, Q, Y, D, E, R, K, H, A, V, L, I, M, W, F or P;

(ai) substitution of L at position 104 or at a position corresponding thereto with S, T, C, Q, Y, D, E, R, K, H, A, V, L, I, M, W, F or P;

(aj) substitution of G at position 105 or at a position corresponding thereto with S, T, C, Q, Y, D, E, R, K, H, A, V, L, I, M, W, F or P;

(ak) substitution of G at position 106 or at a position corresponding thereto with S, T, C, Q, Y, D, E, R, K, H, A, V, L, I, M, W, F or P;

(al) substitution of L at position 107 or at a position corresponding thereto with S, R, K or A;

(m) substitution of S at position 109 or at a position corresponding thereto with L, I or F;

(an) substitution of T at position 113 or at a position corresponding thereto with L or W;

(ao) substitution of Y at position 119 or at a position corresponding thereto with G, S, T, C, N, Q, D, E, R, K, H, A, V, M, W, F or P;

(ap) substitution of S at position 120 or at a position corresponding thereto with Y, R, I, W or F;

(aq) substitution of R at position 124 or at a position corresponding thereto with K or A;

(ar) substitution of A at position 132 or at a position corresponding thereto with S, T, N, Q, D, I or M;

(as) substitution of A at position 133 or at a position corresponding thereto with G, S, T, C, N, Q, D, E, R, K, H, V, L, I, M, W, F or P;

(at) substitution of V at position 134 or at a position corresponding thereto with G, S, T or A;
(au) insertion of G, S, T, N, Q, Y, R, K, H, A, L, I, M or W between the position 133 or a position corresponding thereto and the position 134 or a position corresponding thereto;
(av) substitution of N at position 135 or at a position corresponding thereto with R, A, L or M;
(aw) substitution of G at position 136 or at a position corresponding thereto with S, T, C, Q, Y, D, E, R, K, H, A, V, L, I, M, W, F or P;
(ax) substitution of Y at position 138 or at a position corresponding thereto with G, S, C, N, Q, D, E, R, K, H, A, V, M, W, F or P;
(ay) substitution of T at position 140 or at a position corresponding thereto with L, W or F;
(az) substitution of Y at position 148 or at a position corresponding thereto with G, S, T, C, N, Q, D, E, R, K, H, A, M, W, F or P;
(ba) substitution of K at position 151 or at a position corresponding thereto with F;
(bb) substitution of E at position 163 or at a position corresponding thereto with S, T, N, Q, D, K, H, V, L, I or F;
(bc) substitution of N at position 166 or at a position corresponding thereto with G, V, L, I, W or F;
(bd) substitution of G at position 167 or at a position corresponding thereto with V;
(be) substitution of I at position 170 or at a position corresponding thereto with V or L;
(bf) substitution of S at position 171 or at a position corresponding thereto with G, T, E or A;
(bg) substitution of N at position 187 or at a position corresponding thereto with S;
(bh) substitution of S at position 191 or at a position corresponding thereto with V, L, I, W or F;
(bi) substitution of G at position 193 or at a position corresponding thereto with S, T, C, Q, Y, D, E, R, K, H, A, V, L, I, M, W, F or P;
(bj) substitution of S at position 194 or at a position corresponding thereto with Y, R or K;
(bk) substitution of Y at position 195 or at a position corresponding thereto with G, S, T, C, N, Q, D, E, R, K, H, A, V, L, I, M, W, F or P;
(bl) substitution of N at position 200 or at a position corresponding thereto with W;
(bm) substitution of Q at position 204 or at a position corresponding thereto with S, T, C, N, D, E, R, K, H, V, L, I, M, W or P;
(bn) substitution of F at position 205 or at a position corresponding thereto with S, T, C, N, Q, Y, E, K, H, A, V, L, I, M or W;
(bo) substitution of K at position 212 or at a position corresponding thereto with N, Q, R, V, L or W;
(bp) substitution of F at position 226 or at a position corresponding thereto with Y;
(bq) substitution of S at position 233 or at a position corresponding thereto with L, I or W;
(br) substitution of D at position 237 or at a position corresponding thereto with N;
(bs) substitution of S at position 238 or at a position corresponding thereto with L;
(bt) substitution of N at position 243 or at a position corresponding thereto with Y, L or I;
(bu) substitution of D at position 245 or at a position corresponding thereto with N;
(bv) substitution of S at position 246 or at a position corresponding thereto with Y, V, L, W or F;
(bw) substitution of K at position 247 or at a position corresponding thereto with S, T, C, N, Q, E, H, A, V, L, I, M, W or F;
(bx) substitution of Y at position 248 or at a position corresponding thereto with F;
(by) substitution of Y at position 250 or at a position corresponding thereto with F;
(bz) substitution of M at position 251 or at a position corresponding thereto with G, T, N, Q, D, A, V, L or I;
(ca) substitution of M at position 256 or at a position corresponding thereto with S, T, C, Q, Y, D, E, R, K, H, A, V, L, I, W, F or P;
(cb) substitution of A at position 257 or at a position corresponding thereto with V or I;
(cc) substitution of N at position 264 or at a position corresponding thereto with G, S, T, C, Q, D, E, A, V, L, I or M;
(cd) substitution of V at position 273 or at a position corresponding thereto with G, T or I;
(ce) substitution of N at position 275 or at a position corresponding thereto with L, W or F;
(cf) substitution of G at position 277 or at a position corresponding thereto with V, L, I or F;
(cg) substitution of K at position 281 or at a position corresponding thereto with R;
(ch) substitution of I at position 296 or at a position corresponding thereto with V;
(ci) substitution of G at position 297 or at a position corresponding thereto with L, W or F;
(cj) substitution of N at position 304 or at a position corresponding thereto with S;
(ck) substitution of D at position 313 or at a position corresponding thereto with N;
(cl) substitution of A at position 319 or at a position corresponding thereto with S, T, C, N, Q, Y, D, E, R, K, H, V, L, I, M, W, F or P;
(cm) substitution of Y at position 320 or at a position corresponding thereto with G, T, V, L, I or F;
(cn) substitution of S at position 326 or at a position corresponding thereto with W;
(co) substitution of S at position 330 or at a position corresponding thereto with M, W or F;
(cp) substitution of K at position 332 or at a position corresponding thereto with G, T or V;
(cq) substitution of T at position 334 or at a position corresponding thereto with L;
(cr) substitution of Y at position 335 or at a position corresponding thereto with F;
(cs) substitution of F at position 337 or at a position corresponding thereto with G, S, T, C, Q, R, K, H, A or V;
(ct) substitution of G at position 342 or at a position corresponding thereto with S, T, C, Q, Y, D, E, R, K, H, A, V, L, I, M, W, F or P;
(cu) substitution of K at position 343 or at a position corresponding thereto with T;
(cv) substitution of K at position 346 or at a position corresponding thereto with R;
(cw) substitution of S at position 357 or at a position corresponding thereto with L;
x) substitution of T at position 359 or at a position corresponding thereto with G, S, Q, V, L, I or F;
(cy) substitution of S at position 361 or at a position corresponding thereto with V, I or W;
(cz) substitution of D at position 369 or at a position corresponding thereto with N;
(da) substitution of N at position 376 or at a position corresponding thereto with W;

(db) substitution of T at position 378 or at a position corresponding thereto with L or W;

(dc) substitution of Q at position 379 or at a position corresponding thereto with D, E, R or K;

(dd) substitution of Y at position 380 or at a position corresponding thereto with F;

(de) substitution of F at position 385 or at a position corresponding thereto with Y, M or P;

(df) substitution of T at position 386 or at a position corresponding thereto with A, L, I or M;

(dg) substitution of S at position 387 or at a position corresponding thereto with G, preferably with Q, E, R, K, H, A, V, L, I, M, W or F;

(dh) substitution of N at position 390 or at a position corresponding thereto with G, S, T, Y or F;

(di) substitution of W at position 393 or at a position corresponding thereto with Q;

(dj) substitution of R at position 396 or at a position corresponding thereto with G;

(dk) substitution of F at position 403 or at a position corresponding thereto with T or K;

(dl) substitution of N at position 405 or at a position corresponding thereto with D, V, L, I, W, F or P;

(dm) substitution of A at position 406 or at a position corresponding thereto with V, W or F;

(dn) substitution of P at position 407 or at a position corresponding thereto with G or C;

(do) substitution of Q at position 408 or at a position corresponding thereto with N, Y, I or W;

(dp) substitution of S at position 409 or at a position corresponding thereto with Y or W;

(dq) substitution of T at position 411 or at a position corresponding thereto with A, V, L or P;

(dr) substitution of T at position 427 or at a position corresponding thereto with R or V; and (ds) substitution of V at position 433 or at a position corresponding thereto with L.

The above-described mutations (a) to (ds) may be applied alone as a single use of any one, or may also be applied in combination of any two or more. Preferred examples include: the (ar); a combination of the (as), (at) and (au); the (bk); the (cz); a combination of the (v), (cd), (cx), and (dg); a combination of the (bc) and (bd); a combination of the (e) and (aa); a combination of the (j), (s), (y), (bh), and (dl); a combination of the (e), (v), (aa), (bc), (bd), (bk), (cd), (cx), (cz), and (dg); a combination of the (e), (v), (aa), (ar), (bc), (bd), (bk), (cd), (cx), (cz), and (dg); a combination of the (v), (as), (at), (au), (bc), (bd), (bk), (cd), (cx), (cz), and (dg); a combination of the (j), (s), (v), (y), (as), (at), (au), (bc), (bd), (bh), (bk), (cd), (cx), (cz), (dg), and (dl); a combination of the (v), (aa), (ar), (bc), (bd), (bk), (cd), (cx), (cz), and (dg); a combination of the (v), (as), (at), (au), (bc), (bd), (bk), (cd), (cx), (cz), and (dg); a combination of the (e), (v), (aa), (bc), (bd), (bk), (bm), (cd), (cl), (cx), (cz), and (dg); and a combination of the (v), (as), (at), (au), (bc), (bd), (bj), (bk), (bo), (cd), (cx), (cz), (dc), and (dg).

In the amino acid sequence of the parent alkaline protease of the mutant according to the present invention, it is preferable that the amino acid residue at a position corresponding to position 30 of the amino acid sequence as shown in SEQ ID NO: 2 be aspartic acid, the amino acid residue at a position corresponding to position 68 thereof be histidine, and the amino acid residue at a position corresponding to position 255 thereof be serine. More preferably, the parent alkaline protease of the mutant according to the present invention has the amino acid residues shown in the following Table 1 (ii) at positions c shown in the following Table 1 (i) in the amino acid sequence as shown in SEQ ID NO: 2. The amino acid residues shown in Table 1 are amino acid residues, which are highly conserved among the parent alkaline proteases as exemplified above (Saeki et al., Journal of bioscience and Bioengineering, 2007, 103: 501-508).

TABLE 1

| (i) Position | (ii) Amino acid residue |
| --- | --- |
| 10 | Alanine |
| 18 | Glycine |
| 21 | Glycine |
| 26 | Valine |
| 27 | Alanine |
| 28 | Valine |
| 30 | Aspartic acid |
| 32 | Glycine |
| 43 | Histidine |
| 52 | Alanine |
| 64 | Aspartic acid |
| 66 | Asparagine |
| 68 | Histidine |
| 69 | Glycine |
| 70 | Threonine |
| 71 | Histidine |
| 72 | Valine |
| 73 | Alanine |
| 74 | Glycine |
| 85 | Glycine |
| 87 | Alanine |
| 88 | Proline |
| 92 | Leucine |
| 106 | Glycine |
| 118 | Alanine |
| 129 | Serine |
| 131 | Glycine |
| 145 | Valine |
| 159 | Alanine |
| 161 | Glycine |
| 162 | Asparagine |
| 173 | Proline |
| 182 | Valine |
| 183 | Glycine |
| 184 | Alanine |
| 203 | Alanine |
| 205 | Phenylalanine |
| 206 | Serine |
| 209 | Glycine |
| 222 | Alanine |
| 223 | Proline |
| 224 | Glycine |
| 225 | Threonine |
| 229 | Serine |
| 253 | Glycine |
| 254 | Threonine |
| 255 | Serine |
| 256 | Methionine |
| 257 | Alanine |
| 259 | Proline |
| 261 | Valine |
| 262 | Alanine |
| 263 | Glycine |
| 266 | Alanine |
| 289 | Leucine |
| 297 | Glycine |
| 303 | Glycine |

The parent alkaline protease of the mutant according to the present invention preferably has any of the following enzymatic properties possessed by the alkaline protease consisting of the amino acid sequence as shown in SEQ ID NO: 2 (Patent Literature 1): 1) The alkaline protease has resistance to oxidants, acts in an alkaline condition (pH 8 or more), and is stable. Herein, the phrase "the alkaline protease has resistance to oxidants" means that, after the alkaline protease has been left in a 50 mM hydrogen peroxide (containing 5 mM calcium chloride) solution (20 mM Britton-Robinson buffer, pH 10) at 20° C. for 20 minutes, the residual activity (synthetic substrate method) is 50% or more. 2) When the alkaline protease has been treated at 50° C. at pH 10 for 10 minutes, the residual activity is 80% or more. 3) The alkaline protease is inhibited by diisopropyl fluorophosphate (DFP) and phenylmethanesulfonyl fluoride (PMSF). 4) The molecular weight is 43,000±2,000 according to SDS-PAGE. The parent alkaline protease more preferably has all of the above-described enzymatic properties 1) to 4).

The parent alkaline protease of the alkaline protease mutant according to the present invention preferably has alanine at a position corresponding to position 294 of the amino acid sequence as shown in SEQ ID NO: 2.

Preferred examples of the parent alkaline protease of the mutant according to the present invention include an alkaline protease consisting of the amino acid sequence as shown in any of SEQ ID NOS: 2 to 11. The amino acid sequences as shown in SEQ ID NOS: 3, 4, 5, 6, 7, 8, 9, 10 and 11 have an identity of 99.8%, 97.7%, 97.5%, 97.5%, 96.3%, 97.7%, 97.5%, 97.2% and 96.8%, respectively, to the amino acid sequence as shown in SEQ ID NO: 2. It is to be noted that the amino acid residues in the amino acid sequences as shown in SEQ ID NOS: 3 to 11, which correspond to alanine at position 294 in the amino acid sequence as shown in SEQ ID NO: 2, are alanine at position 294 (SEQ ID NOS: 3 to 5, 8, and 10) and alanine at position 295 (SEQ ID NOS: 6, 7, 9, and 11).

The alkaline protease mutant according to the present invention can be produced by substituting the amino acid residue at a position corresponding to position 294 of the amino acid sequence as shown in SEQ ID NO: 2 with threonine, in the amino acid sequence of the aforementioned parent alkaline protease. Accordingly, in the alkaline protease mutant according to the present invention, the amino acid residue at a position corresponding to position 294 of the amino acid sequence as shown in SEQ ID NO: 2 is threonine. The alkaline protease mutant according to the present invention has an improved stability to a chelating agent, in comparison to the parent alkaline protease thereof. Therefore, in comparison to the parent alkaline protease, the alkaline protease mutant according to the present invention is more stable in a chelating agent-containing solution, for example, in a detergent solution, and, as a result, can retain a higher alkaline protease activity in the chelating agent-containing solution.

Preferably, in the alkaline protease mutant according to the present invention, the amino acid residue at a position corresponding to position 294 of the amino acid sequence as shown in SEQ ID NO: 2 is threonine, and the sequence identity thereof is at least 95% to the amino acid sequence as shown in SEQ ID NO: 2. More preferably, in the alkaline protease mutant according to the present invention the sequence identity thereof is at least 95% to the amino acid sequence as shown in SEQ ID NO: 2, the amino acid residue at a position corresponding to position 294 of the amino acid sequence as shown in SEQ ID NO: 2 is threonine, the amino acid residue at a position corresponding to position 30 of the amino acid sequence as shown in SEQ ID NO: 2 is aspartic acid, the amino acid residue at a position corresponding to position 68 thereof is histidine, and the amino acid residue at a position corresponding to position 255 thereof is serine.

Among the aforementioned parent alkaline proteases, the amino acid residue at a position corresponding to position 294 of the amino acid sequence as shown in SEQ ID NO: 2 is considered to be present at a position equivalent to the alanine at position 294 of the alkaline protease as shown in SEQ ID NO: 2 in the three-dimensional structure of these proteins. Accordingly, it is assumed that mutations in the amino acid residues present at positions corresponding to the position 294 in the parent alkaline protease would have effects similar to one another on their specific functions.

Besides, when one amino acid residue is inserted into the parent alkaline protease, as in the case of the aforementioned (au), the position corresponding to the position after position 134 in SEQ ID NO: 2 of the parent alkaline protease is located downstream by one residue, compared with SEQ ID NO: 2.

In addition to the aforementioned mutation at a position corresponding to the position 294, the alkaline protease mutant according to the present invention may also have a mutation (e.g., a deletion, substitution, addition or insertion) at any other position in the parent alkaline protease, as long as such a mutation does not impair a stability-improving effect in a chelating agent-containing solution. This mutation may be either a naturally occurring mutation, or an artificially introduced mutation.

For example, the alkaline protease mutant according to the present invention may have one or more amino acid residues selected from the group consisting of the substituted amino acid residues described in the above (a) to (ds). For example, the alkaline protease mutant according to the present invention may have the following amino acid residue(s) the substituted amino acid residue described in the (ar); the substituted amino acid residue described in the (as), (at) and (au); the substituted amino acid residue described in the (bk); the substituted amino acid residue described in the (cz); the substituted amino acid residue described in the (v), (cd), (cx) and (dg); the substituted amino acid residue described in the (bc) and (bd); the substituted amino acid residue described in the (e) and (aa); the substituted amino acid residue described in the (j), (s), (y), (bh) and (dl); the substituted amino acid residue described in the (e), (v), (aa), (bc), (bd), (bk), (cd), (cx), (cz) and (dg); the substituted amino acid residue described in the (e), (v), (aa), (ar), (bc), (bd), (bk), (cd), (cx), (cz) and (dg); the substituted amino acid residue described in the (v), (as), (at), (au), (bc), (bd), (bk), (cd), (cx), (cz) and (dg); the substituted amino acid residue described in the (j), (s), (v), (y), (as), (at), (au), (bc), (bd), (bh), (bk), (cd), (cx), (cz), (dg) and (dl); the substituted amino acid residue described in the (v), (aa), (ar), (bc), (bd), (bk), (cd), (cx), (cz) and (dg); the substituted amino acid residue described in the (v), (as), (at), (au), (bc), (bd), (bk), (cd), (cx), (cz) and (dg); the substituted amino acid residue described in the (e), (v), (aa), (bc), (bd), (bk), (bm), (cd), (cl), (cx), (cz) and (dg); or the substituted amino acid residue described in the (v), (as), (at), (au), (bc), (bd), (bj), (bk), (bo), (cd), (cx), (cz), (dc) and (dg). These alkaline protease mutants may be obtained by substituting the alanine at a position corresponding to position 294 of the amino acid sequence as shown in SEQ ID NO: 2 with threonine, in the parent alkaline protease having any one or more mutations described in the above (a) to (ds). Alternatively, these alkaline protease mutants may also be obtained by introducing any one or more mutations described in the above (a) to (ds), as well as the A294T mutation, into the parent alkaline protease of the amino acid sequence as shown in SEQ ID NO: 2.

Examples of the alkaline protease mutant according to the present invention include an A294T mutant of alkaline protease consisting of the amino acid sequence as shown in any of SEQ ID NOS: 2 to 5, 8, and 10, and an A295T mutant of alkaline protease consisting of the amino acid sequence as shown in any of SEQ ID NOS: 6, 7, 9, and 11.

In the present invention, as a means for mutating the amino acid residue(s) in the parent alkaline protease, various types of mutation introduction techniques, which have been known in the present technical field, can be used. For instance, in a polynucleotide encoding the amino acid sequence of the parent alkaline protease (hereinafter also referred to as a "parent gene"), a nucleotide sequence encoding an amino acid residue to be mutated is mutated to a nucleotide sequence encoding the mutated amino acid residue, and a protein is then allowed to express from the mutant gene, so that an alkaline protease mutant of interest can be obtained.

Basically, introduction of a mutation of interest into a parent gene can be carried out, for example, by performing various site-directed mutagenesis methods, which are well known to a person skilled in the art, based on PCR amplification using the parent gene as template DNA or a replication reaction using various types of DNA polymerases. Such a site-directed mutagenesis method can be carried out, for example, by applying any method such as an inverse PCR method or an annealing method (edited by Muramatsu et al., "Revised 4th edition, "New Gene Engineering Handbook", Yodosha, pp. 82-88). It is also possible to use various types of commercially available kits for site-directed mutagenesis, such as Quick Change II Site-Directed Mutagenesis Kit or Quick Change Multi Site-Directed Mutagenesis Kit from Stratagene.

The site-directed mutagenesis into the parent gene can be carried out, most commonly, using mutation primers containing a nucleotide mutation to be introduced. The mutation primers may be designed, such that they anneal to a region containing a nucleotide sequence encoding an amino acid residue to be mutated in a parent gene, and contain a nucleotide sequence having a nucleotide sequence (codon) encoding the mutated amino acid residue, instead of a nucleotide sequence (codon) encoding the amino acid residue to be mutated. A person skilled in the art could appropriately recognize and select nucleotide sequences (codons) encoding the unmutated and mutated amino acid residues, based on a common textbook and the like. Alternatively, the site-directed mutagenesis can be carried out by a method of using separately two primers complementary to each other containing a nucleotide mutation to be introduced to amplify DNA fragments of an upstream side and a downstream side of a mutation site and ligating the DNA fragments into one fragment, according to SOE (splicing by overlap extension)—PCR (Horton et al, Gene, 1989, 77(1): pp. 61-68).

A template DNA containing a parent gene can be prepared from bacteria such as the aforementioned *Bacillus* sp. KSM-KP43 (FERM BP-6532), *Bacillus* sp. KSM-KP9860 (FERM BP-6534) or *Bacillus* sp. KSM-9865 (FERM P-18566), or mutant strains thereof by extracting genomic DNA therefrom according to a common method, or by extracting RNA therefrom and then synthesizing cDNA by reverse transcription. Alternatively, based on the amino acid sequence of the parent alkaline protease, the corresponding nucleotide sequence may be chemically synthesized, and may be then used as the template DNA.

Preparation of genomic DNA from such a strain of *Bacillus* sp. can be carried out, for example, by applying the method described in Pitcher et al, Lett Appl Microbiol, 1989, 8: 151-156 and the like. Template DNA containing a parent gene may be prepared in a form in which the prepared cDNA, or a DNA fragment containing a parent gene cleaved from genomic DNA is inserted into any vector.

Mutation primers can be produced according to a publicly known oligonucleotide synthetic method, such as a phosphoramidite method (Nucleic Acids Research, 1989, 17: 7059-7071). Such primer synthesis can also be carried out, for example, using a commercially available oligonucleotide synthesizing apparatus (manufactured by ABI, etc.). The site-directed mutagenesis as described above is carried out using a parent gene as a template DNA and using a primer set including the mutation primers, so that an alkaline protease mutant gene, into which a mutation of interest has been introduced, can be obtained.

Accordingly, the present invention also provides an alkaline protease mutant gene. The alkaline protease mutant gene according to the present invention is a polynucleotide encoding the alkaline protease mutant according to the present invention. The polynucleotide according to the present invention may include single-stranded or double-stranded DNA, cDNA, RNA, and other artificial nucleic acids. The DNA, cDNA and RNA may also be chemically synthesized. Further, the polynucleotide according to the present invention may contain a nucleotide sequence of an untranslated region (UTR), in addition to an open reading frame (ORF).

The present invention also provides a vector containing the polynucleotide encoding the alkaline protease mutant according to the present invention. The vector can be produced by inserting the polynucleotide according to the present invention into any vector, and thus ligating them according to a common method. The type of the vector is not particularly limited, and it may be any vector such as a plasmid, a phage, a phagemid, a cosmid, a virus, a YAC vector or a shuttle vector. Moreover, the vector is preferably a vector capable of amplifying in bacteria, particularly in bacteria of *Bacillus* sp., more preferably an expression vector capable of inducing expression of an introduced gene in bacteria of *Bacillus* sp., although the vector is not limited thereto. Among them, a shuttle vector, which is replicable in any of bacteria of *Bacillus* sp. and another organism, can be preferably used in recombination production of the alkaline protease mutant according to the present invention. Examples of a preferred vector include, but are not limited to: shuttle vectors such as pHA3040SP64, pHSP64R or pASP64 (JP-B-3492935), pHY300PLK (an expression vector capable of transforming both *Escherichia coli* and *Bacillus subtilis*; Ishikawa and Shibahara, Jpn J Genet, 1985, 60: 235-243), and pAC3 (Moriyama et al, Nucleic Acids Res, 1988, 16: 8732); plasmids available for transformation of bacteria of *Bacillus* sp. such as pUB110 (Gryczan et al, J Bacteriol, 1978, 134: 318-329) or pTA10607 (Bron et al, Plasmid, 1987, 18: 8-15); and secretion vectors capable of giving secretion signals to recombinant proteins (Yamane et al., "Fusion Proteins Using *Bacillus subtilis* Secretion Vectors," Starch Science, 34. (1987), 163-170). Furthermore, *Escherichia coli*-derived plasmids (e.g., pET22b(+), pBR322, pBR325, pUC118, pUC119, pUC18, pUC19, pBluescript, etc.) can also be used.

When the alkaline protease mutant according to the present invention is produced by recombination, the vector is preferably an expression vector. The expression vector may contain, as necessary, useful sequences including various types of elements essential for expression in host organisms, such as a transcription promoter, a terminator, or a ribosome-binding site; cis-elements such as a polylinker or an enhancer; poly A addition signal; a ribosome binding sequence (SD sequence); and selective marker genes such as a drug (e.g., ampicillin, neomycin, kanamycin, tetracycline, chloramphenicol, etc.) resistant gene.

The present invention further provides a transformant containing a polynucleotide encoding the alkaline protease mutant according to the present invention or a vector containing such a polynucleotide. The transformant can be produced by introducing a polynucleotide encoding the alkaline protease mutant according to the present invention or a vector containing such a polynucleotide (preferably, a recombinant expression vector) into a host.

Examples of a host for the transformant include: bacteria such as *Escherichia coli* or *Bacillus subtilis*; microorganisms including yeast cells as typical examples; and any cells such as insect cells, animal cells (e.g., mammalian cells), or plant cells. The host is preferably a bacterium of *Bacillus* sp., more preferably *Bacillus subtilis* or a mutant strain thereof. Therefore, the transformant according to the present invention is a recombinant bacterium of *Bacillus* sp., and more preferably a recombinant *Bacillus subtilis* or a mutant strain thereof.

For transformation of a host, publicly known transformation techniques, such as a calcium phosphate method, an electroporation method, a lipofection method, a particle gun method, or a PEG method, can be applied. Examples of a transformation method applicable to bacteria of *Bacillus* sp., include a competent cell transformation method (J Bacteriol, 1967, 93: 1925-1937), an electroporation method (Brigidi et al, FEMS Microbiol Lett, 1990, 55: 135-138), a protoplast transformation method (Chang and Cohen, Mol Gen Genet, 1979, 168: 111-115), and a Tris-PEG method (Takahashi et al, J Bacteriol, 1983, 156: 1130-1134).

The alkaline protease mutant according to the present invention can be produced by culturing the transformant according to the present invention. Accordingly, the present invention also provides a method for producing an alkaline protease mutant including, using the transformant according to the present invention. The transformant for production of an alkaline protease mutant can be cultured according to a common method well known to a person skilled in the art. For instance, a medium used to culture a transformant based on a microorganism host such as *Escherichia coli* or yeast cells may be a medium which contained therein a carbon source, a nitrogen source, inorganic salts, etc. capable of being assimilated by the microorganism host, and in which the transformant can be efficiently cultured therein. The medium used herein may be either a natural medium or a synthetic medium. For instance, for the culture of a *Bacillus subtilis* transformant to produce a recombinant protein, an LB medium, a 2×YT medium, a 2×L-maltose medium, a CSL fermentation medium or the like can be used. To such a medium, a drug which corresponds to the type of a drug resistant gene (selective marker gene) introduced into the transformant, may be added. In addition, in the case of culturing microorganisms transformed with an expression vector using an inducible promoter, an inducer may be added to the medium, as necessary. For example, in the case of culturing microorganisms transformed with an expression vector using a Lac promoter, isopropyl-1-thio-β-D-galactoside (IPTG), etc. can be added to the medium. In the case of culturing microorganisms transformed with an expression vector using a trp promoter, indoleacetic acid (IAA), etc. can be added to the medium.

Alternatively, the alkaline protease mutant according to the present invention may be expressed from a polynucleotide encoding the alkaline protease mutant according to the present invention or a transcriptional product thereof, using a cell-free translation system. The "cell-free translation system" refers to an in vitro transcription translation system or an in vitro translation system, which is obtained by adding reagents necessary for translation of proteins, such as amino acids, to a suspension obtained by mechanically homogenizing cells serving as a host.

The alkaline protease mutant according to the present invention produced in the aforementioned transformant or cell-free translation system can be obtained from a culture solution, a cell-homogenized solution, a reaction solution of the cell-free translation system, etc., by applying common methods used in protein purification, such as centrifugation, ammonium sulfate precipitation, gel chromatography, ion exchange chromatography, and affinity chromatography alone or in appropriate combination. Alternatively, a solution separated or concentrated using centrifugation, an ultrafiltration filter and the like, such as a culture supernatant or a lysate supernatant, can be directly used as a crude enzyme solution. When the expressed alkaline protease mutant is not secreted from cells, the cells may be homogenized, and then, separation and purification of proteins may be carried out.

Experiments used in the present invention, such as preparation of mRNA, production of cDNA, PCR, RT-PCR, production of a library, ligation into a vector, transformation of cells, determination of DNA base sequence, chemical synthesis of nucleic acids, determination of amino acid sequence on the N-terminal side of a protein, mutagenesis, and extraction of a protein, can be carried out according to methods described in ordinary experimental manuals. Examples of such an experimental manual include Sambrook et al., Molecular Cloning, A laboratory manual, 2001, 3rd Ed., Sambrook, J. & Russell, DW., Cold Spring Harbor Laboratory Press. Moreover, in the case of an experiment regarding genetic recombination of *Bacillus subtilis*, common experimental manuals for genetic engineering of *Bacillus subtilis* such as Hirofumi Yoshikawa, "7.2 *Bacillus subtilis* system," "Continued Biochemical Experiment Seminar 1. Genetic Research Method II," 1986, Tokyo Kagaku Dojin Co., Ltd. (Tokyo), pp. 150-169, etc., can be referred to, for example.

The alkaline protease mutant obtained by the production method according to the present invention has an improved stability to a chelating agent, in comparison to the parent alkaline protease thereof, and thus, the present alkaline protease mutant can be more stably present in a chelating agent-containing solution, preferably in a liquid detergent. Accordingly, another aspect of the present invention may be a method for improving the stability of alkaline protease to a chelating agent, including substituting the amino acid residue at a position corresponding to position 294 of the amino acid sequence as shown in SEQ ID NO: 2, in the amino acid sequence of the aforementioned parent alkaline protease.

Since the alkaline protease mutant according to the present invention has high stability to a chelating agent, it is useful as an enzyme to be mixed into a detergent. A detergent containing the alkaline protease mutant according to the present invention can maintain higher protease activity than conventional detergents, and as a result, it can exhibit stronger enzyme detergency. Accordingly, the present invention also provides a detergent composition containing the alkaline protease mutant according to the present invention. This detergent composition may be a powdery detergent composition, but it is preferably a liquid detergent composition.

The detergent composition according to the present invention contains a chelating agent. Examples of the chelating agent which can be contained in the detergent composition according to the present invention are the same as those described above. The content of the chelating agent in the detergent composition according to the present invention is preferably from 0.1% to 5% by mass, more preferably from 0.1% to 4% by mass.

The content of the alkaline protease mutant according to the present invention in the detergent composition according to the present invention is not particularly limited, as long as the alkaline protease exhibits its activity. The content of the alkaline protease mutant according to the present invention is preferably from 0.1 to 25000 U, more preferably from 0.1 to 5000 U, further preferably from 0.1 to 2500 U, based on 1 kg of the detergent composition. Besides, the activity (U) of the alkaline protease is measured by the following method. That is, 0.9 mL of 1/15 M phosphate buffer (pH 7.4) and 0.05 mL of 40 mM Glt-Ala-Ala-Pro-Leu-p-nitroanilide/dimethyl sulfoxide solution are added into a test tube, and are then kept warm at 30° C. for 5 minutes. To the obtained mixture, 0.05 mL of enzyme solution is added, followed by performing a reaction at 30° C. for 10 minutes. Thereafter, 2.0 mL of 5% (w/v) citric acid aqueous solution is added to the reaction solution to terminate the reaction, and the absorbance at 420 nm is then measured using a spectrophotometer. Herein, 1 unit (U) of enzyme is defined to be an amount of enzyme necessary for producing 1 μmol p-nitroaniline for 1 minute in the above described reaction.

The detergent composition according to the present invention contains a surfactant and water, in addition to the alkaline protease mutant according to the present invention. As such surfactants, any surfactants such as an anionic surfactant, a nonionic surfactant, an amphoteric surfactant, and a cationic surfactant can be used alone or in combination of two or more types. The content of the surfactant in the detergent composition according to the present invention is preferably from 10% to 80% by mass, more preferably from 30% to 70% by mass.

The nonionic surfactant may be a nonionic surfactant having a C8 to C22 hydrocarbon group and with several moles or more of C2 oxyalkylene groups added, which is generally mixed into a liquid detergent, and examples of such a nonionic surfactant include:

$R_1$O-(AO)m-H (wherein $R_1$=C8 to C22 hydrocarbon, AO=C2 to C5 oxyalkylene group, and m=16 to 35) [JP-A-2010-275468];

$R_1$O-(EO)l-(AO)m-(EO)n-H (wherein $R_1$=C8 to C18 hydrocarbon, EO=C2 oxyalkylene group, AO=C3 to C5 oxyalkylene group, l=3 to 30, m=1 to 5, and 1+n=14 to 50) [JP-A-2010-265445, JP-A-2011-63784];

$R_1$O-(EO)m/(AO)n-H (wherein $R_1$=C8 to C22 hydrocarbon, EO=C2 oxyalkylene group, AO=C3 to C5 oxyalkylene group, m=10 to 30, n=0 to 5, and EO and AO are random or block bonds) [JP-A-2010-189551];

$R_1$(CO)lO-(EO) m/(AO)n-$R_2$ (wherein $R_1$=C8 to C22 hydrocarbon, EO=C2 oxyalkylene group, AO=C3 to C5 oxyalkylene group, l=0 to 1, m=14 to 50, n=1 to 5, $R_2$=hydrogen (l=0) or C1 to C3 alkyl group, and EO and AO are random or block bonds) [JP-A-2010-229385];

$R_1$O-(EO)m-(AO)n-H (wherein $R_1$=C8 to C22 hydrocarbon, EO=C2 oxyalkylene group, AO=C3 to C5 oxyalkylene group, m=15 to 30, and n=1 to 5) [JP-A-2010-229387];

$R_1$O-(AO)m/(Gly)n-H and/or $R_2$—COO-(AO)p/(Gly)q-H (wherein $R_1$=C8 to C22 hydrocarbon group, $R_2$=C7 to C21 hydrocarbon group, AO=C2 to C3 oxyalkylene group, Gly=glycerol group, m=0 to 5, n=2 to 10, p=0 to 5, q=2 to 10, and AO and Gly are random or block bonds) [JP-A-2010-254881];

$R_1$—COO—(PO)m/(EO)n-$R_2$ (wherein $R_1$=C7 to C21 hydrocarbon group, COO=carbonyloxy group, $R_2$=C1 to C3 alkyl group, PO=oxypropylene group, BO=oxyethylene group, m=0.3 to 5, n=8 to 25, and PO and EO are random or block bonds) [JP-A-2010-265333];

$R_1$O-(EO) l-(PO)m-(EO)n-H (wherein $R_1$=C8 to C20 hydrocarbon, EO=C2 oxyalkylene group, PO=oxypropylene group, 1>=1, n>=1, 0<m<1+n, and EO and PO are block bonds) [WO98/24865];

$R_1$O-(EO)m-(PO)n-H (wherein $R_1$=C10 to C16 alkyl group or alkenyl group, EO=ethyleneoxide group, PO=propyleneoxide group, m=5 to 15, and n=1 to 3) [JP-A-8-157867];

$R_1$(CO)-(EO)m-O$R_2$ (wherein $R_1$=C11 to C13 linear or branched alkyl group or alkenyl group, $R_2$=C1 to C3 alkyl group, EO=ethyleneoxide group, and m=10 to 20) [JP-A-2008-7706, JP-A-2009-7451, JP-A-2009-155594, and JP-A-2009-155606];

$R_1$(CO)-(AO)m-O$R_2$ (wherein $R_1$=C9 to C13 linear or branched alkyl group or alkenyl group, AO=C2 to C4 oxyalkylene group, $R_2$=C1 to C3 alkyl group, m=5 to 30) [JP-A-2009-144002, JP-A-2009-173858, and JP-A-2010-189612]; and fatty acid alkanolamide, fatty acid alkanol glucamide, and alkyl polyglucoside.

Examples of the anionic surfactant include a carboxylate-type anionic surfactant, a sulfonate-type or sulfate-type anionic surfactant, a nonsoap anionic surfactant, linear alkylbenzenesulfonic acid, benzenesulfonic acid or a salt thereof, polyoxybenzenesulfonic acid or a salt thereof, a polyoxyethylene alkyl sulfate salt, a polyoxyalkylene alkyl ether sulfate salt, α-olefin sulfonate, alkyl benzenesulfonate, α-sulfo fatty acid salt, fatty acid soap, a phosphate-based surfactant, acyl alaninate, acyl taurate, alkyl ether carboxylic acid, and alcohol sulfate.

Examples of the cationic surfactant include a quaternary ammonium salt having a long-chain alkyl group, a tertiary amine having one long-chain alkyl group, an alkyltrimethylammonium salt, a dialkyldimethylammonium salt, and an alkyl pyridinium salt. Preferred examples of the cationic surfactant include a quaternary ammonium-type surfactant having one long-chain alkyl group having 8 to 22 carbon atoms, and a tertiary amine having one long-chain alkyl group having 8 to 22 carbon atoms.

Examples of the amphoteric surfactant include alkylbetaine-type, alkylamidobetaine-type, imidazoline-type, alkylaminosulfone-type, alkylaminocarboxylic acid-type, alkylamidocarboxylic acid-type, and amidoamino acid-type or phosphoric acid-type amphoteric surfactants, such as alkylacetic acid betaine, alkanolamido propyl acetic acid betaine, alkyl imidazoline, and alkyl alanine. A preferred example of the amphoteric surfactant is sulfobetaine or carbobetaine having an alkyl group having 10 to 18 carbon atoms.

The detergent composition according to the present invention may further contain components commonly used in a detergent composition, such as, for example, a water-soluble polymer, a water-miscible organic solvent, an alkaline agent, organic acid or a salt thereof, an enzyme other than the alkaline protease mutant according to the present invention, an enzyme stabilizer, a fluorescent agent, an anti-refouling agent, a dispersant, a color migration inhibitor, a finishing agent, a bleaching agent such as hydrogen peroxide, an antioxidant, a solubilizer, a pH adjuster, a buffer, an antiseptic, a perfume, a salt, alcohol, and sugars.

Examples of the water-soluble polymer include: a polymer compound, having (i) a polyether chain moiety containing a polymerized unit derived from an epoxide having 2 to 5 carbon atoms, and (ii) a polymer chain moiety containing a polymerized unit derived from one or more unsaturated carboxylic acid monomers selected from the group consisting of acrylic acid, methacrylic acid and maleic acid, and having a graft structure in which either (i) or (ii) is a main chain, and the other is a branched chain (JP-A-2010-275468 and JP-A-10-060496); and a water-soluble polymer having an alkylene terephthalate unit and/or an alkylene isophthalate unit, and an oxyalkylene unit and/or a polyoxyalkylene unit (JP-A-2009-155606). The content of the water-soluble polymer in the detergent composition according to the present invention is preferably from 0.2% to 10% by mass, more preferably from 0.4% to 5% by mass.

Examples of the water-miscible organic solvent include alkanols such as alkylene glycols or glycerin, polyalkylene glycols, (poly)alkylene glycol (mono or di)alkyl ethers, alkyl glyceryl ethers, and aromatic ethers of (poly)alkylene glycol. Preferred examples of the water-miscible organic solvent include alkylene glycols having from 2 to 6 carbon atoms, such as ethylene glycol, propylene glycol, butylene glycol or hexylene glycol, glycerin, polyethylene glycol monophenyl ether, ethylene glycol monobenzyl ether, and diethylene glycol monobenzyl ether. The content of the water-miscible organic solvent in the detergent composition according to the present invention is preferably from 1% to 40% by mass, more preferably from 1% to 35% by mass.

Examples of the alkaline agent include alkanolamines having one to three C2 to C4 alkanols, such as monoethanolamine, diethanolamine, triethanolamine, polyoxyalkyleneamine, or dimethylaminopropylamine. Among these, monoethanolamine and triethanolamine are preferable. The content of the alkaline agent in the detergent composition according to the present invention is preferably from 0% to 20% by mass, more preferably from 0% to 10% by mass.

Examples of the organic acid or a salt thereof include: polyvalent carboxylic acids such as saturated fatty acid, succinic acid, maleic acid, and fumaric acid, or their salts; and hydroxycarboxylic acids such as citric acid, malic acid, glycolic acid, and p-hydroxybenzoic acid, or their salts. Among these, citric acid or salt thereof is preferable. The content of the organic acid or a salt thereof in the detergent composition according to the present invention is preferably from 0% to 5% by mass, more preferably from 0% to 3% by mass.

Examples of the anti-refouling agent and the dispersant include anti-refouling agents and dispersers such as polyacrylic acid, polymaleic acid, carboxymethyl cellulose, polyethylene glycol having a weight average molecular weight of 5000 or more, a maleic anhydride-diisobutylene copolymer, a maleic anhydride-methyl vinyl ether copolymer, a maleic anhydride-vinyl acetate copolymer, a naphthalene sulfonate formalin condensate, and polymers recited in claims 1 to 21 of JP-A-59-62614 (page 1, column 3, line 5 to page 3, column 4, line 14). However, if such anti-refouling agents and dispersants are not suitable to be mixed into the detergent composition of the present invention, these agents may be excluded.

The color migration inhibitor is, for example, polyvinyl pyrrolidone. The content of the color migration inhibitor in the detergent composition according to the present invention is preferably from 0.01% to 10% by mass.

A bleaching agent such as hydrogen peroxide, percarbonate or perborate is added in an amount of 1% to 10% by mass into the present detergent composition. In the case of using such a bleaching agent, tetraacetylethylenediamine (TAED) or a bleaching activator (activator) described in JP-A-6-316700, etc., can be added in an amount of from 0.01% to 10% by mass into the detergent composition.

Examples of the fluorescent agent include a biphenyl-type fluorescent agent (Tinopal CBS-X, etc.) and a stilbene-type fluorescent agent (DM-type fluorescent dye, etc.). The content of the fluorescent agent in the detergent composition according to the present invention is preferably from 0.001 to 2% by mass.

Examples of the enzyme other than the alkaline protease mutant according to the present invention include hydrolytic enzymes such as other proteases, cellulase, β-glucanase, hemicellulase, lipase, peroxidase, laccase, α-amylase, glucoamylase, cutinase, pectinase, reductase, oxidase, phenol oxidase, ligninase, pullulanase, pectate lyase, xyloglucanase, xylanase, pectin acetyl esterase, polygalacturonase, rhamnogalacturonase, pectin lyase, mannanase, pectin methyl esterase, cellobiohydrolase and transglutaminase, and a mixture of two or more of these enzymes.

Examples of the enzyme stabilizer include a boron compound, a calcium ion source (a calcium ion-supplying compound), a hydroxy compound, and formic acid. Examples of the antioxidant include butylhydroxytoluene, distyrenated cresol, sodium sulfite, and sodium hydrogen sulfite. Examples of the solubilizer include p-toluenesulfonic acid, cumenesulfonic acid, m-xylenesulfonic acid, and benzoate (which also has an effect as an antiseptic). Furthermore, the detergent composition according to the present invention may also contain: water-immiscible organic solvents including paraffins such as octane, decane, dodecane or tridecane, olefins such as decene or dodecene, halogenated alkyls such as methylene chloride or 1,1,1-trichloroethane, and terpenes such as D-limonene; pigments; perfumes; antibacterial-antiseptic agents; and antifoaming agents such as silicone.

Preferred examples of a detergent composition which can contain the alkaline protease mutant according to the present invention include the liquid detergent compositions described in the Examples of JP-A-2010-265333, JP-A-2014-141662, JP-A-2009-191128, JP-A-2012-224652, JP-A-2013-503950, and JP-A-11-512768. For example, the detergent composition according to the present invention can be prepared by mixing the alkaline protease mutant according to the present invention into the liquid detergent composition described in Example 4 of JP-A-2014-141662 [i.e., a composition containing 30% of surfactants (20% of an anionic surfactant and 10% of a nonionic surfactant), 3% of citric acid, 18% of an organic solvent having a hydroxyl group (diethylene glycol monobutyl ether), an alkaline agent (monoethanolamine) necessary for adjusting the pH of the composition to pH 8.0, ion exchange water, perfume, etc.].

The detergent composition according to the present invention is not limited to, but is preferably used for washing clothes or fabrics (sheets, curtains, carpets, wall clothes, etc.). Since the detergent composition according to the present invention can stably maintain the alkaline protease mutant according to the present invention, it can exhibit high enzyme detergency.

The present invention also includes, as illustrative embodiments, the following substances, production methods, intended uses, methods, etc. However, the present invention is not limited to these embodiments.

[1] An alkaline protease mutant consisting of an amino acid sequence obtained by substituting an amino acid residue at a position corresponding to position 294 in the amino acid sequence as shown in SEQ ID NO:2 with threonine in the amino acid sequence as shown in SEQ ID NO:2 or an amino acid sequence having an identity of at least 95% thereto.

[2] The alkaline protease mutant according to the above [1], wherein the amino acid sequence as shown in SEQ ID NO: 2, or the amino acid sequence having an identity of at least 95% thereto preferably has alanine at a position corresponding to position 294 of the amino acid sequence as shown in SEQ ID NO: 2.

[3] The alkaline protease mutant according to the above [1] or [2], wherein the amino acid sequence having an identity of at least 95% to the amino acid sequence as shown in SEQ ID NO: 2 is preferably the amino acid sequence of protease KP9860 or protease 9865.

[4] The alkaline protease mutant according to any one of the above [1] to [3], wherein the amino acid sequence having an identity of at least 95% to the amino acid sequence as shown in SEQ ID NO: 2

(i) preferably has one or more amino acid residues selected from the group consisting of the following (a') to (ds'):

(a') the amino acid residue at position 6 of the amino acid sequence as shown in SEQ ID NO: 2 or at a position corresponding thereto, which is S, T, C, Q, Y, R, K, H, A, V, L, I, M, W or F;

(b') the amino acid residue at position 9 of the amino acid sequence as shown in SEQ ID NO: 2 or at a position corresponding thereto, which is Q;

(c') the amino acid residue at position 11 of the amino acid sequence as shown in SEQ ID NO: 2 or at a position corresponding thereto, which is G, S or N;

(d') the amino acid residue at position 15 of the amino acid sequence as shown in SEQ ID NO: 2 or at a position corresponding thereto, which is H, C, Q, D, E, R, A, V, M, W or F;

(e') the amino acid residue at position 16 of the amino acid sequence as shown in SEQ ID NO: 2 or at a position corresponding thereto, which is T, Q, V, C, Y, D, E, R, K, H, L, I, M, W or F;

(f') the amino acid residue at position 20 of the amino acid sequence as shown in SEQ ID NO: 2 or at a position corresponding thereto, which is F or A;

(g') the amino acid residue at position 22 of the amino acid sequence as shown in SEQ ID NO: 2 or at a position corresponding thereto, which is W;

(h') the amino acid residue at position 23 of the amino acid sequence as shown in SEQ ID NO: 2 or at a position corresponding thereto, which is N;

(i') the amino acid residue at position 37 of the amino acid sequence as shown in SEQ ID NO: 2 or at a position corresponding thereto, which is T;

(j') the amino acid residue at position 40 of the amino acid sequence as shown in SEQ ID NO: 2 or at a position corresponding thereto, which is V, L, I, W or F;

(k') the amino acid residue at position 41 of the amino acid sequence as shown in SEQ ID NO: 2 or at a position corresponding thereto, which is I;

(l') the amino acid residue at position 46 of the amino acid sequence as shown in SEQ ID NO: 2 or at a position corresponding thereto, which is S, T, C, N, Q, Y, E, K, H, A, V, L, I, M or W;

(m') the amino acid residue at position 49 of the amino acid sequence as shown in SEQ ID NO: 2 or at a position corresponding thereto, which is Q;

(n') the amino acid residue at position 52 of the amino acid sequence as shown in SEQ ID NO: 2 or at a position corresponding thereto, which is G or S;

(o') the amino acid residue at position 53 of the amino acid sequence as shown in SEQ ID NO: 2 or at a position corresponding thereto, which is A, V or I;

(p') the amino acid residue at position 54 of the amino acid sequence as shown in SEQ ID NO: 2 or at a position corresponding thereto, which is G, S, T, C, N, Q, D, E, R, H, A, V, M, W, F or P;

(q') the amino acid residue at position 56 of the amino acid sequence as shown in SEQ ID NO: 2 or at a position corresponding thereto, which is V;

(r') the amino acid residue at position 57 of the amino acid sequence as shown in SEQ ID NO: 2 or at a position corresponding thereto, which is S, T, C, Q, D, E, R, K, H, A, V, L, I, M, W, or P;

(s') the amino acid residue at position 59 of the amino acid sequence as shown in SEQ ID NO: 2 or at a position corresponding thereto, which is V, L, I, M, W or F;

(t') the amino acid residue at position 60 of the amino acid sequence as shown in SEQ ID NO: 2 or at a position corresponding thereto, which is V, L, I, W or F;

(u') the amino acid residue at position 63 of the amino acid sequence as shown in SEQ ID NO: 2 or at a position corresponding thereto, which is S, D or L;

(v') the amino acid residue at position 65 of the amino acid sequence as shown in SEQ ID NO: 2 or at a position corresponding thereto, which is W or P;

(w') the amino acid residue at position 66 of the amino acid sequence as shown in SEQ ID NO: 2 or at a position corresponding thereto, which is G, S, T, C, Q, D, E, H, A, V, L, I, M or W;

(x') the amino acid residue at position 80 of the amino acid sequence as shown in SEQ ID NO: 2 or at a position corresponding thereto, which is H or A;

(y') the amino acid residue at position 81 of the amino acid sequence as shown in SEQ ID NO: 2 or at a position corresponding thereto, which is Q, Y, L, I, W or F;

(z') the amino acid residue at position 82 of the amino acid sequence as shown in SEQ ID NO: 2 or at a position corresponding thereto, which is G, S, C, Q, D, E, R, K, H, A or M;

(aa') the amino acid residue at position 83 of the amino acid sequence as shown in SEQ ID NO: 2 or at a position corresponding thereto, which is S, C or A;

(ab') the amino acid residue at position 84 of the amino acid sequence as shown in SEQ ID NO: 2 or at a position corresponding thereto, which is R;

(ac') the amino acid residue at position 89 of the amino acid sequence as shown in SEQ ID NO: 2 or at a position corresponding thereto, which is H;

(ad') the amino acid residue at position 91 of the amino acid sequence as shown in SEQ ID NO: 2 or at a position corresponding thereto, which is C;

(ae') the amino acid residue at position 100 of the amino acid sequence as shown in SEQ ID NO: 2 or at a position corresponding thereto, which is L, I, W or F;

(af') the amino acid residue at position 101 of the amino acid sequence as shown in SEQ ID NO: 2 or at a position corresponding thereto, which is S, T, C, N, Q, Y, D, E, R, K, H, A, V, L, I, M, W, F or P;

(ag') the amino acid residue at position 102 of the amino acid sequence as shown in SEQ ID NO: 2 or at a position corresponding thereto, which is S, T, C, Q, Y, D, E, R, K, H, A, V, L, I, M, W, F or P;

(ah') the amino acid residue at position 103 of the amino acid sequence as shown in SEQ ID NO: 2 or at a position corresponding thereto, which is S, T, C, Q, Y, D, E, R, K, H, A, V, L, I, M, W, F or P;

(ai') the amino acid residue at position 104 of the amino acid sequence as shown in SEQ ID NO: 2 or at a position corresponding thereto, which is S, T, C, Q, Y, D, E, R, K, H, A, V, L, I, M, W, F or P;

(aj') the amino acid residue at position 105 of the amino acid sequence as shown in SEQ ID NO: 2 or at a position corresponding thereto, which is S, T, C, Q, Y, D, E, R, K, H, A, V, L, I, M, W, F or P;

(ak') the amino acid residue at position 106 of the amino acid sequence as shown in SEQ ID NO: 2 or at a position corresponding thereto, which is S, T, C, Q, Y, D, E, R, K, H, A, V, L, I, M, W, F or P;

(al') the amino acid residue at position 107 of the amino acid sequence as shown in SEQ ID NO: 2 or at a position corresponding thereto, which is S, R, K or A;

(am') the amino acid residue at position 109 of the amino acid sequence as shown in SEQ ID NO: 2 or at a position corresponding thereto, which is L, I or F;

(an') the amino acid residue at position 113 of the amino acid sequence as shown in SEQ ID NO: 2 or at a position corresponding thereto, which is L or W;

(ao') the amino acid residue at position 119 of the amino acid sequence as shown in SEQ ID NO: 2 or at a position corresponding thereto, which is G, S, T, C, N, Q, D, E, R, K, H, A, V, M, W, F or P;

(ap') the amino acid residue at position 120 of the amino acid sequence as shown in SEQ ID NO: 2 or at a position corresponding thereto, which is Y, R, I, W or F;

(aq') the amino acid residue at position 124 of the amino acid sequence as shown in SEQ ID NO: 2 or at a position corresponding thereto, which is K or A;

(ar') the amino acid residue at position 132 of the amino acid sequence as shown in SEQ ID NO: 2 or at a position corresponding thereto, which is S, T, N, Q, D, I or M;

(as') the amino acid residue at position 133 of the amino acid sequence as shown in SEQ ID NO: 2 or at a position corresponding thereto, which is G, S, T, C, N, Q, D, E, R, K, H, V, L, I, M, W, F or P;

(at') the amino acid residue at position 134 of the amino acid sequence as shown in SEQ ID NO: 2 or at a position corresponding thereto, which is G, S, T or A;

(au') the amino acid residue between position 133 of the amino acid sequence as shown in SEQ ID NO: 2 or a position corresponding thereto, and position 134 thereof or a position corresponding thereto, which is G, S, T, N, Q, Y, R, K, H, A, L, I, M or W;

(av') the amino acid residue at position 135 of the amino acid sequence as shown in SEQ ID NO: 2 or at a position corresponding thereto, which is R, A, L or M;

(aw') the amino acid residue at position 136 of the amino acid sequence as shown in SEQ ID NO: 2 or at a position corresponding thereto, which is S, T, C, Q, Y, D, E, R, K, H, A, V, L, I, M, W, F or P;

(ax') the amino acid residue at position 138 of the amino acid sequence as shown in SEQ ID NO: 2 or at a position corresponding thereto, which is G, S, C, N, Q, D, E, R, K, H, A, V, M, W, F or P;

(ay') the amino acid residue at position 140 of the amino acid sequence as shown in SEQ ID NO: 2 or at a position corresponding thereto, which is L, W or F;

(az') the amino acid residue at position 148 of the amino acid sequence as shown in SEQ ID NO: 2 or at a position corresponding thereto, which is G, S, T, C, N, Q, D, E, R, K, H, A, M, W, F or P;

(ba') the amino acid residue at position 151 of the amino acid sequence as shown in SEQ ID NO: 2 or at a position corresponding thereto, which is F;

(bb') the amino acid residue at position 163 of the amino acid sequence as shown in SEQ ID NO: 2 or at a position corresponding thereto, which is S, T, N, Q, D, K, H, V, L, I or F;

(bc') the amino acid residue at position 166 of the amino acid sequence as shown in SEQ ID NO: 2 or at a position corresponding thereto, which is G, V, L, I, W or F;

(bd') the amino acid residue at position 167 of the amino acid sequence as shown in SEQ ID NO: 2 or at a position corresponding thereto, which is V;

(be') the amino acid residue at position 170 of the amino acid sequence as shown in SEQ ID NO: 2 or at a position corresponding thereto, which is V or L;

(bf) the amino acid residue at position 171 of the amino acid sequence as shown in SEQ ID NO: 2 or at a position corresponding thereto, which is G, T, E or A;

(bg') the amino acid residue at position 187 of the amino acid sequence as shown in SEQ ID NO: 2 or at a position corresponding thereto, which is S;

(bh') the amino acid residue at position 191 of the amino acid sequence as shown in SEQ ID NO: 2 or at a position corresponding thereto, which is V, L, I, W or F;

(bi') the amino acid residue at position 193 of the amino acid sequence as shown in SEQ ID NO: 2 or at a position corresponding thereto, which is S, T, C, Q, Y, D, E, R, K, H, A, V, L, I, M, W, F or P;

(bj') the amino acid residue at position 194 of the amino acid sequence as shown in SEQ ID NO: 2 or at a position corresponding thereto, which is Y, R or K;

(bk') the amino acid residue at position 195 of the amino acid sequence as shown in SEQ ID NO: 2 or at a position corresponding thereto, which is G, S, T, C, N, Q, D, E, R, K, H, A, V, L, I, M, W, F or P;

(bl') the amino acid residue at position 200 of the amino acid sequence as shown in SEQ ID NO: 2 or at a position corresponding thereto, which is W;

(bm') the amino acid residue at position 204 of the amino acid sequence as shown in SEQ ID NO: 2 or at a position corresponding thereto, which is S, T, C, N, D, E, R, K, H, V, L, I, M, W or P;

(bn') the amino acid residue at position 205 of the amino acid sequence as shown in SEQ ID NO: 2 or at a position corresponding thereto, which is S, T, C, N, Q, Y, E, K, H, A, V, L, I, M or W;

(bo') the amino acid residue at position 212 of the amino acid sequence as shown in SEQ ID NO: 2 or at a position corresponding thereto, which is N, Q, R, V, L or W;

(bp') the amino acid residue at position 226 of the amino acid sequence as shown in SEQ ID NO: 2 or at a position corresponding thereto, which is Y;

(bq') the amino acid residue at position 233 of the amino acid sequence as shown in SEQ ID NO: 2 or at a position corresponding thereto, which is L, I or W;

(br') the amino acid residue at position 237 of the amino acid sequence as shown in SEQ ID NO: 2 or at a position corresponding thereto, which is N;

(bs') the amino acid residue at position 238 of the amino acid sequence as shown in SEQ ID NO: 2 or at a position corresponding thereto, which is L;

(bt') the amino acid residue at position 243 of the amino acid sequence as shown in SEQ ID NO: 2 or at a position corresponding thereto, which is Y, L or I;

(bu') the amino acid residue at position 245 of the amino acid sequence as shown in SEQ ID NO: 2 or at a position corresponding thereto, which is N;

(by') the amino acid residue at position 246 of the amino acid sequence as shown in SEQ ID NO: 2 or at a position corresponding thereto, which is V, L, W or F;

(bw') the amino acid residue at position 247 of the amino acid sequence as shown in SEQ ID NO: 2 or at a position corresponding thereto, which is S, T, C, N, Q, E, H, A, V, L, I, M W or F;

(bx') the amino acid residue at position 248 of the amino acid sequence as shown in SEQ ID NO: 2 or at a position corresponding thereto, which is F;

(by') the amino acid residue at position 250 of the amino acid sequence as shown in SEQ ID NO: 2 or at a position corresponding thereto, which is F;

(bz') the amino acid residue at position 251 of the amino acid sequence as shown in SEQ ID NO: 2 or at a position corresponding thereto, which is G, T, N, Q, D, A, V, L or I;

(ca') the amino acid residue at position 256 of the amino acid sequence as shown in SEQ ID NO: 2 or at a position corresponding thereto, which is S, T, C, Q, Y, D, E, R, K, H, A, V, L, I, W, F or P;

(cb') the amino acid residue at position 257 of the amino acid sequence as shown in SEQ ID NO: 2 or at a position corresponding thereto, which is V or I;

(cc') the amino acid residue at position 264 of the amino acid sequence as shown in SEQ ID NO: 2 or at a position corresponding thereto, which is G, 5, T, C, Q, D, E, A, V, L, I or M;

(cd') the amino acid residue at position 273 of the amino acid sequence as shown in SEQ ID NO: 2 or at a position corresponding thereto, which is G, T or I;

(ce') the amino acid residue at position 275 of the amino acid sequence as shown in SEQ ID NO: 2 or at a position corresponding thereto, which is L, W or F;

(cf') the amino acid residue at position 277 of the amino acid sequence as shown in SEQ ID NO: 2 or at a position corresponding thereto, which is V, L, I or F;

(cg') the amino acid residue at position 281 of the amino acid sequence as shown in SEQ ID NO: 2 or at a position corresponding thereto, which is R;

(ch') the amino acid residue at position 296 of the amino acid sequence as shown in SEQ ID NO: 2 or at a position corresponding thereto, which is V;

(ci') the amino acid residue at position 297 of the amino acid sequence as shown in SEQ ID NO: 2 or at a position corresponding thereto, which is L, W or F;

(cj') the amino acid residue at position 304 of the amino acid sequence as shown in SEQ ID NO: 2 or at a position corresponding thereto, which is S;

(ck') the amino acid residue at position 313 of the amino acid sequence as shown in SEQ ID NO: 2 or at a position corresponding thereto, which is N;

(cl') the amino acid residue at position 319 of the amino acid sequence as shown in SEQ ID NO: 2 or at a position corresponding thereto, which is S, T, C, N, Q, Y, D, E, R, K, H, V, L, I, M, W, F or P;

(cm') the amino acid residue at position 320 of the amino acid sequence as shown in SEQ ID NO: 2 or at a position corresponding thereto, which is G, T, V, L, I or F;

(cn') the amino acid residue at position 326 of the amino acid sequence as shown in SEQ ID NO: 2 or at a position corresponding thereto, which is W;

(co') the amino acid residue at position 330 of the amino acid sequence as shown in SEQ ID NO: 2 or at a position corresponding thereto, which is M, W or F;

(cp') the amino acid residue at position 332 of the amino acid sequence as shown in SEQ ID NO: 2 or at a position corresponding thereto, which is G, T or V;

(cq') the amino acid residue at position 334 of the amino acid sequence as shown in SEQ ID NO: 2 or at a position corresponding thereto, which is L;

(cr') the amino acid residue at position 335 of the amino acid sequence as shown in SEQ ID NO: 2 or at a position corresponding thereto, which is F;

(cs') the amino acid residue at position 337 of the amino acid sequence as shown in SEQ ID NO: 2 or at a position corresponding thereto, which is G, S, T, C, Q, R, K, H, A or V;

(ct') the amino acid residue at position 342 of the amino acid sequence as shown in SEQ ID NO: 2 or at a position corresponding thereto, which is S, T, C, Q, Y, D, E, R, K, H, A, V, L, I, M, W, F or P;

(cu') the amino acid residue at position 343 of the amino acid sequence as shown in SEQ ID NO: 2 or at a position corresponding thereto, which is T;

(cv') the amino acid residue at position 346 of the amino acid sequence as shown in SEQ ID NO: 2 or at a position corresponding thereto, which is R;

(cw') the amino acid residue at position 357 of the amino acid sequence as shown in SEQ ID NO: 2 or at a position corresponding thereto, which is L;

(cx') the amino acid residue at position 359 of the amino acid sequence as shown in SEQ ID NO: 2 or at a position corresponding thereto, which is G, S, Q, V, L, I or F;

(cy') the amino acid residue at position 361 of the amino acid sequence as shown in SEQ ID NO: 2 or at a position corresponding thereto, which is V, I or W;

(cz') the amino acid residue at position 369 of the amino acid sequence as shown in SEQ ID NO: 2 or at a position corresponding thereto, which is N;

(da') the amino acid residue at position 376 of the amino acid sequence as shown in SEQ ID NO: 2 or at a position corresponding thereto, which is W;

(db') the amino acid residue at position 378 of the amino acid sequence as shown in SEQ ID NO: 2 or at a position corresponding thereto, which is L or W;

(dc') the amino acid residue at position 379 of the amino acid sequence as shown in SEQ ID NO: 2 or at a position corresponding thereto, which is D, E, R or K;

(dd') the amino acid residue at position 380 of the amino acid sequence as shown in SEQ ID NO: 2 or at a position corresponding thereto, which is F;

(de') the amino acid residue at position 385 of the amino acid sequence as shown in SEQ ID NO: 2 or at a position corresponding thereto, which is Y, M or P;

(df') the amino acid residue at position 386 of the amino acid sequence as shown in SEQ ID NO: 2 or at a position corresponding thereto, which is A, L, I or M;

(dg') the amino acid residue at position 387 of the amino acid sequence as shown in SEQ ID NO: 2 or at a position corresponding thereto, which is G, Q, E, R, K, H, A, V, L, I, M, W or F;

(dh') the amino acid residue at position 390 of the amino acid sequence as shown in SEQ ID NO: 2 or at a position corresponding thereto, which is G, S, T, Y or F;

(di') the amino acid residue at position 393 of the amino acid sequence as shown in SEQ ID NO: 2 or at a position corresponding thereto, which is Q;

(dj') the amino acid residue at position 396 of the amino acid sequence as shown in SEQ ID NO: 2 or at a position corresponding thereto, which is G;

(dk') the amino acid residue at position 403 of the amino acid sequence as shown in SEQ ID NO: 2 or at a position corresponding thereto, which is T or K;

(dl') the amino acid residue at position 405 of the amino acid sequence as shown in SEQ ID NO: 2 or at a position corresponding thereto, which is D, V, L, I, W, F or P;

(dm') the amino acid residue at position 406 of the amino acid sequence as shown in SEQ ID NO: 2 or at a position corresponding thereto, which is V, W or F;

(dn') the amino acid residue at position 407 of the amino acid sequence as shown in SEQ ID NO: 2 or at a position corresponding thereto, which is G or C;

(do') the amino acid residue at position 408 of the amino acid sequence as shown in SEQ ID NO: 2 or at a position corresponding thereto, which is N, Y, I or W;

(dp') the amino acid residue at position 409 of the amino acid sequence as shown in SEQ ID NO: 2 or at a position corresponding thereto, which is Y or W;

(dq') the amino acid residue at position 411 of the amino acid sequence as shown in SEQ ID NO: 2 or at a position corresponding thereto, which is A, V, L or P;

(dr') the amino acid residue at position 427 of the amino acid sequence as shown in SEQ ID NO: 2 or at a position corresponding thereto, which is R or V; and (ds') the amino acid residue at position 433 of the amino acid sequence as shown in SEQ ID NO: 2 or at a position corresponding thereto, which is L,
and
(ii) more preferably has any of the following:
the amino acid residue described in (ar');
the amino acid residues described in (as'), (at'), and (au');
the amino acid residue described in (bk');
the amino acid residue described in (cz');
the amino acid residues described in (v'), (cd'), (cx'), and (dg');
the amino acid residues described in (be'), and (bd');
the amino acid residues described in (e'), and (aa');
the amino acid residues described in (j'), (s'), (y'), (bh'), and (dl');
the amino acid residues described in (e'), (v'), (aa'), (bc'), (bd'), (bk'), (cd'), (cx'), (cz'), and (dg');
the amino acid residues described in (e'), (v'), (aa'), (ar'), (bc'), (bd'), (bk'), (cd'), (cx'), (cz'), and (dg');
the amino acid residues described in (v'), (as'), (at'), (au'), (bc'), (bd'), (bk'), (cd'), (cx'), (cz'), and (dg');
the amino acid residues described in (j'), (s'), (v'), (y'), (as'), (at'), (a (bc'), (bd'), (bh'), (bk'), (cd'), (cx'), (cz'), (dg'), and (dl');
the amino acid residues described in (v'), (aa'), (ar'), (bc'), (bd'), (bk'), (cd'), (cx'), (cz'), and (dg');
the amino acid residues described in (v'), (as'), (at'), (au'), (bc'), (bd'), (bk'), (cd'), (cx'), (cz'), and (dg');
the amino acid residues described in (e'), (v'), (aa'), (bc'), (bd'), (bk'), (bm'), (cd'), (cl'), (cx'), (cz'), and (dg'); and
the amino acid residues described in (v'), (as'), (at'), (au), (be'), (bd'), (bj'), (bk'), (bo') (cd'), (cx'), (cz'), (dc'), and (dg').

[5] The alkaline protease mutant according to any one of the above [1] to [4], wherein
the amino acid sequence having an identity of at least 95% to the amino acid sequence as shown in SEQ ID NO: 2 preferably has aspartic acid at a position corresponding to position 30 of the amino acid sequence as shown in SEQ ID NO: 2, histidine at a position corresponding to position 68 thereof, and serine at a position corresponding to position 255 thereof,
more preferably has the amino acid residues shown in the aforementioned Table 1 (ii) at positions corresponding to the positions shown in the aforementioned Table 1 (i) in the amino acid sequence as shown in SEQ ID NO: 2.

[6] The alkaline protease mutant according to any one of the above [1] to [5], which is preferably an A294T mutant of an alkaline protease mutant consisting of the amino acid sequence shown in any of SEQ ID NOS: 2 to 5, 8, and 10, or an A295T mutant of an alkaline protease mutant consisting of the amino acid sequence shown in any of SEQ ID NOS: 6, 7, 9, and 11.

[7] A polynucleotide encoding the alkaline protease mutant according to any one of the above [1] to [6].

[8] A vector comprising the polynucleotide according to the above [7].

[9] A transformant comprising the polynucleotide according to the above [7] or the vector according to the above [8], which is a foreign matter.

[10] The vector according to the above [8] or the transformant according to the above [9], wherein the vector is preferably an expression vector capable of inducing expression of an introduced gene in a bacterium of *Bacillus* sp.

[11] The transformant according to the above [9] or [10], which is preferably a recombinant bacterium of *Bacillus* sp.

[12] A method for producing an alkaline protease mutant, using the transformant according to any one of the above [9] to [11].

[13] A detergent composition comprising the alkaline protease mutant according to any one of the above [1] to [6].

[14] The detergent composition according to the above [13], preferably comprising a chelating agent.

[15] The detergent composition according to the above [13] or [14], which is preferably a liquid detergent composition.

[16] The detergent composition according to the above [15], wherein the content of a surfactant is preferably from 10% to 80% by mass, more preferably from 30% to 70% by mass.

[17] A method for producing an alkaline protease mutant, comprising substituting the amino acid residue at a position corresponding to position 294 of the amino acid sequence as shown in SEQ ID NO: 2 with threonine, in the amino acid sequence as shown in SEQ ID NO: 2, or an amino acid sequence having an identity of at least 95% thereto.

[18] A method for improving stability of alkaline protease to a chelating agent, comprising substituting the amino acid residue at a position corresponding to position 294 of the amino acid sequence as shown in SEQ ID NO: 2 with threonine, in the amino acid sequence as shown in SEQ ID NO: 2, or an amino acid sequence having an identity of at least 95% thereto.

[19] The method according to the above [17] or [18], wherein the amino acid sequence having an identity of at least 95% to the amino acid sequence as shown in SEQ ID NO: 2 preferably has alanine at a position corresponding to position 294 of the amino acid sequence as shown in SEQ ID NO: 2.

[20] The method according to any one of the above [17] to [19], wherein the amino acid sequence having an identity of at least 95% to the amino acid sequence as shown in SEQ ID NO: 2 is preferably the amino acid sequence of protease KP9860 or protease 9865.

[21] The method according to any one of the above [17] to [19], wherein the amino acid sequence having an identity of at least 95% to the amino acid sequence as shown in SEQ ID NO: 2 is preferably an amino acid sequence having the following mutation(s) in the amino acid sequence as shown in SEQ ID NO: 2:

(i) preferably, one or more mutations selected from the group consisting of the following mutations (a) to (ds):
(a) substitution of G at position 6 or at a position corresponding thereto with S, T, C, Q, Y, R, K, H, A, V, L, I, M, W or F;
(b) substitution of K at position 9 or at a position corresponding thereto with Q;
(c) substitution of D at position 11 or at a position corresponding thereto with G, S or N;
(d) substitution of S at position 15 or at a position corresponding thereto with H, C, Q, D, E, R, A, V, M, W or F;
(e) substitution of S at position 16 or at a position corresponding thereto with T, Q, V, C, Y, D, E, R, K, H, L, I, M, W or F;
(f) substitution of Y at position 20 or at a position corresponding thereto with F or A;
(g) substitution of Q at position 22 or at a position corresponding thereto with W;
(h) substitution of G at position 23 or at a position corresponding thereto with N;
(i) substitution of R at position 37 or at a position corresponding thereto with T;
(j) substitution of S at position 40 or at a position corresponding thereto with V, L, I, W or F;
(k) substitution of S at position 41 or at a position corresponding thereto with I;
(l) substitution of F at position 46 or at a position corresponding thereto with S, T, C, N, Q, Y, E, K, H, A, V, L, I, M or W;
(m) substitution of K at position 49 or at a position corresponding thereto with Q;
(n) substitution of A at position 52 or at a position corresponding thereto with G or S;
(o) substitution of L at position 53 or at a position corresponding thereto with A, V or I;
(p) substitution of Y at position 54 or at a position corresponding thereto with G, S, T, C, N, Q, D, E, R, H, A, V, M, W, F or P;
(q) substitution of L at position 56 or at a position corresponding thereto with V;
(r) substitution of G at position 57 or at a position corresponding thereto with S, T, C, Q, D, E, R, K, H, A, V, L, I, M, W, F or P;
(s) substitution of T at position 59 or at a position corresponding thereto with V, L, I, M, W or F;
(t) substitution of N at position 60 or at a position corresponding thereto with V, L, I, W or F;
(u) substitution of N at position 63 or at a position corresponding thereto with S, D or L;
(v) substitution of T at position 65 or at a position corresponding thereto with W or P;
(w) substitution of N at position 66 or at a position corresponding thereto with G, S, T, C, Q, D, E, H, A, V, L, I, M or W;
(x) substitution of G at position 80 or at a position corresponding thereto with H or A;
(y) substitution of S at position 81 or at a position corresponding thereto with Q, Y, L, I, W or F;
(z) substitution of T at position 82 or at a position corresponding thereto with G, S, C, Q, D, E, R, K, H, A or M;
(aa) substitution of N at position 83 or at a position corresponding thereto with S, C or A;
(ab) substitution of K at position 84 or at a position corresponding thereto with R;
(ac) substitution of Q at position 89 or at a position corresponding thereto with H;
(ad) substitution of N at position 91 or at a position corresponding thereto with C;
(ae) substitution of S at position 100 or at a position corresponding thereto with L, I, W or F;
(af) substitution of G at position 101 or at a position corresponding thereto with S, T, C, N, Q, Y, D, E, R, K, H, A, V, L, I, M, W, F or P;
(ag) substitution of G at position 102 or at a position corresponding thereto with S, T, C, Q, Y, D, E, R, K, H, A, V, L, I, M, W, F or P;
(ah) substitution of G at position 103 or at a position corresponding thereto with S, T, C, Q, Y, D, E, R, K, H, A, V, L, I, M, W, F or P;
(ai) substitution of L at position 104 or at a position corresponding thereto with S, T, C, Q, Y, D, E, R, K, H, A, V, L, I, M, W, F or P;
(aj) substitution of G at position 105 or at a position corresponding thereto with S, T, C, Q, Y, D, E, R, K, H, A, V, L, I, M, W, F or P;
(ak) substitution of G at position 106 or at a position corresponding thereto with S, T, C, Q, Y, D, E, R, K, H, A, V, L, I, M, W, F or P;
(al) substitution of L at position 107 or at a position corresponding thereto with S, R, K or A;
(am) substitution of S at position 109 or at a position corresponding thereto with L, I or F;
(an) substitution of T at position 113 or at a position corresponding thereto with L or W;
(ao) substitution of Y at position 119 or at a position corresponding thereto with G, S, T, C, N, Q, D, E, R, K, H, A, V, M, W, F or P;
(ap) substitution of S at position 120 or at a position corresponding thereto with Y, R, I, W or F;
(aq) substitution of R at position 124 or at a position corresponding thereto with K or A;
(ar) substitution of A at position 132 or at a position corresponding thereto with S, T, N, Q, D, I or M;
(as) substitution of A at position 133 or at a position corresponding thereto with G, S, T, C, N, Q, D, E, R, K, H, V, L, I, M, W, F or P;
(at) substitution of V at position 134 or at a position corresponding thereto with G, S, T or A;
(au) insertion of G, S, T, N, Q, Y, R, K, H, A, L, I, M or W into a site between the position 133 or a position corresponding thereto and the position 134 or a position corresponding thereto;
(av) substitution of N at position 135 or at a position corresponding thereto with R, A, L or M;
(aw) substitution of G at position 136 or at a position corresponding thereto with S, T, C, Q, Y, D, E, R, K, H, A, V, L, I, M, W, F or P;
(ax) substitution of Y at position 138 or at a position corresponding thereto with G, S, C, N, Q, D, E, R, K, H, A, V, M, W, F or P;
(ay) substitution of T at position 140 or at a position corresponding thereto with L, W or F;
(az) substitution of Y at position 148 or at a position corresponding thereto with G, S, T, C, N, Q, D, E, R, K, H, A, M, W, F or P;
(ba) substitution of K at position 151 or at a position corresponding thereto with F;
(bb) substitution of E at position 163 or at a position corresponding thereto with S, T, N, Q, D, K, H, V, L, I or F;
(bc) substitution of N at position 166 or at a position corresponding thereto with G, V, L, I, W or F;
(bd) substitution of G at position 167 or at a position corresponding thereto with V;

(be) substitution of I at position 170 or at a position corresponding thereto with V or L;
(bf) substitution of S at position 171 or at a position corresponding thereto with G, T, E or A;
(bg) substitution of N at position 187 or at a position corresponding thereto with S;
(bh) substitution of S at position 191 or at a position corresponding thereto with V, L, I, W or F;
(bi) substitution of G at position 193 or at a position corresponding thereto with S, T, C, Q, Y, D, E, R, K, H, A, V, L, I, M, W, F or P;
(bj) substitution of S at position 194 or at a position corresponding thereto with Y, R or K;
(bk) substitution of Y at position 195 or at a position corresponding thereto with G, S, T, C, N, Q, D, E, R, K, H, A, V, L, I, M, W, F or P;
(bl) substitution of N at position 200 or at a position corresponding thereto with W;
(bm) substitution of Q at position 204 or at a position corresponding thereto with S, T, C, N, D, E, R, K, H, V, L, I, M, W or P;
(bn) substitution of F at position 205 or at a position corresponding thereto with S, T, C, N, Q, Y, E, K, H, A, V, L, I, M or W;
(bo) substitution of K at position 212 or at a position corresponding thereto with N, Q, R, V, L or W;
(bp) substitution of F at position 226 or at a position corresponding thereto with Y;
(bq) substitution of S at position 233 or at a position corresponding thereto with L, I or W;
(br) substitution of D at position 237 or at a position corresponding thereto with N;
(bs) substitution of S at position 238 or at a position corresponding thereto with L;
(bt) a substitution of N at position 243 or at a position corresponding thereto with Y, L or I;
(bu) substitution of D at position 245 or at a position corresponding thereto with N;
(by) substitution of S at position 246 or at a position corresponding thereto with Y, V, L, W or F;
(bw) substitution of K at position 247 or at a position corresponding thereto with S, T, C, N, Q, E, H, A, V, L, I, M, W or F;
(bx) substitution of Y at position 248 or at a position corresponding thereto with F;
(by) substitution of Y at position 250 or at a position corresponding thereto with F;
(bz) substitution of M at position 251 or at a position corresponding thereto with G, T, N, Q, D, A, V, L or I;
(ca) substitution of M at position 256 or at a position corresponding thereto with S, T, C, Q, Y, D, E, R, K, H, A, V, L, I, W, F or P;
(cb) substitution of A at position 257 or at a position corresponding thereto with V or I;
(cc) substitution of N at position 264 or at a position corresponding thereto with G, S, T, C, Q, D, E, A, V, L, I or M;
(cd) substitution of V at position 273 or at a position corresponding thereto with G, T or I;
(ce) substitution of N at position 275 or at a position corresponding thereto with L, W or F;
(cf) substitution of G at position 277 or at a position corresponding thereto with V, L, I or F;
(cg) substitution of K at position 281 or at a position corresponding thereto with R;
(ch) substitution of I at position 296 or at a position corresponding thereto with V;
(ci) substitution of G at position 297 or at a position corresponding thereto with L, W or F;
(cj) substitution of N at position 304 or at a position corresponding thereto with S;
(ck) substitution of D at position 313 or at a position corresponding thereto with N;
(cl) substitution of A at position 319 or at a position corresponding thereto with S, T, C, N, Q, Y, D, E, R, K, H, V, L, I, M, W, F or P;
(cm) substitution of Y at position 320 or at a position corresponding thereto with G, T, V, L, I or F;
(cn) substitution of S at position 326 or at a position corresponding thereto with W;
(co) substitution of S at position 330 or at a position corresponding thereto with M, W or F;
(cp) substitution of K at position 332 or at a position corresponding thereto with G, T or V;
(cq) substitution of T at position 334 or at a position corresponding thereto with L;
(cr) substitution of Y at position 335 or at a position corresponding thereto with F;
(cs) substitution of F at position 337 or at a position corresponding thereto with G, S, T, C, Q, R, K, H, A or V;
(ct) substitution of G at position 342 or at a position corresponding thereto with S, T, C, Q, Y, D, E, R, K, H, A, V, L, I, M, W, F or P;
(cu) substitution of K at position 343 or at a position corresponding thereto with T;
(cv) substitution of K at position 346 or at a position corresponding thereto with R;
(cw) substitution of S at position 357 or at a position corresponding thereto with L;
(cx) substitution of T at position 359 or at a position corresponding thereto with G, S, Q, V, L, I or F;
(cy) substitution of S at position 361 or at a position corresponding thereto with V, I or W;
(cz) substitution of D at position 369 or at a position corresponding thereto with N;
(da) substitution of N at position 376 or at a position corresponding thereto with W;
(db) substitution of T at position 378 or at a position corresponding thereto with L or W;
(dc) substitution of Q at position 379 or at a position corresponding thereto with D, E, R or K;
(dd) substitution of Y at position 380 or at a position corresponding thereto with F;
(de) substitution of F at position 385 or at a position corresponding thereto with Y, M or P;
(df) substitution of T at position 386 or at a position corresponding thereto with A, L, I or M;
(dg) substitution of S at position 387 or at a position corresponding thereto with G, Q, E, R, K, H, A, V, L, I, M, W or F;
(dh) substitution of N at position 390 or at a position corresponding thereto with G, S, T, Y or F;
(di) substitution of W at position 393 or at a position corresponding thereto with Q;
(dj) substitution of R at position 396 or at a position corresponding thereto with G;
(dk) substitution of F at position 403 or at a position corresponding thereto with T or K;
(dl) substitution of N at position 405 or at a position corresponding thereto with D, V, L, I, W, F or P;
(dm) substitution of A at position 406 or at a position corresponding thereto with V, W or F;
(dn) substitution of P at position 407 or at a position corresponding thereto with G or C;

(do) substitution of Q at position 408 or at a position corresponding thereto with N, Y, I or W;
(dp) substitution of S at position 409 or at a position corresponding thereto with Y or W;
(dq) substitution of T at position 411 or at a position corresponding thereto with A, V, L or P;
(dr) substitution of T at position 427 or at a position corresponding thereto with R or V; and
(ds) substitution of V at position 433 or at a position corresponding thereto with L,
(ii) more preferably, any of the following:
(ar);
a combination of (as), (at), and (au);
(bk);
(cz);
a combination of (v), (cd), (cx), and (dg);
a combination of (bc) and (bd);
a combination of (e) and (aa);
a combination of (j), (s), (y), (bh), and (dl);
a combination of (e), (v), (aa), (bc), (bd), (bk), (cd), (cx), (cz), and (dg);
a combination of (e), (v), (aa), (ar), (bc), (bd), (bk), (cd), (cx), (cz), and (dg);
a combination of (v), (as), (at), (au), (bc), (bd), (bk), (cd), (cx), (cz), and (dg);
a combination of (j), (s), (v), (y), (as), (at), (au), (bc), (bd), (bh), (bk), (cd), (cx), (cz), (dg), and (dl);
a combination of (v), (aa), (ar), (bc), (bd), (bk), (cd), (cx), (cz), and (dg);
a combination of (v), (as), (at), (au), (bc), (bd), (bk), (cd), (cx), (cz), and (dg);
a combination of (e), (v), (aa), (bc), (bd), (bk), (bm), (cd), (cl), (cx), (cz), and (dg); and
a combination of (v), (as), (at), (au), (bc), (bd), (bj), (bk), (bo), (cd), (cx), (cz), (dc), and (dg).

[22] The method according to any one of the above [17] to [21], wherein
the amino acid sequence having an identity of at least 95% to the amino acid sequence as shown in SEQ ID NO: 2 preferably has aspartic acid at a position corresponding to position 30 of the amino acid sequence as shown in SEQ ID NO: 2, histidine at a position corresponding to position 68 thereof, and serine at a position corresponding to position 255 thereof,
more preferably has the amino acid residues shown in the aforementioned (ii) of Table 1 at positions corresponding to the positions shown in the aforementioned (i) of Table 1 in the amino acid sequence as shown in SEQ ID NO: 2.

[23] The method according to any one of the above [17] to [22], wherein the amino acid sequence as shown in SEQ ID NO: 2 or the amino acid sequence having an identity of at least 95% thereto is preferably the amino acid sequence shown in any of SEQ ID NOS: 2 to 11.

EXAMPLES

Hereinafter, the present invention will be more specifically described in the following examples. However, these examples are not intended to limit the technical scope of the present invention.

Example 1 Production of Alkaline Protease Mutant

The method for producing the alkaline protease mutant according to the present invention will be described below, using, as an example, the production of an "A294T" mutant, in which the alanine at position 294 (A294) in the amino acid sequence (SEQ ID NO: 2) of a wild-type KP43 protease mature enzyme region has been substituted with threonine.

Site-directed mutagenesis was introduced into a recombinant vector containing a *Bacillus* sp. KSM-KP43 strain-derived alkaline protease structural gene (SEQ ID NO: 1) encoding the alkaline protease as shown in SEQ ID NO: 2, by substituting the amino acid residue at position 294 of SEQ ID NO: 2 with threonine. Mutation primers, namely, A294-F (SEQ ID NO: 12: GGTGCAACTGACATCGGC-CTTGGCTAC) and A294-R (SEQ ID NO: 13: GATGTCA-GTTGCACCGGCAATCAGTGC) were designed. Using these primers, a mutation-introduced PCR product was obtained in accordance with the protocols of PrimeSTAR Mutagenesis Basal Kit (Takara). The PCR product was purified with a PCR product purification kit (Roche), and a *Bacillus* sp. KSM9865 strain (FERM P-18566) used as a host bacterium was then transformed therewith.

The obtained transformant was allowed to grow in a skimmed milk-containing alkaline agar medium [1% (w/v) skimmed milk (Difco), 1% bactotripton (Difco), 0.5% yeast extract (Difco), 1% sodium chloride, 1.5% agar, 0.05% sodium carbonate, and 15 ppm tetracycline], and thereafter, the presence or absence of a mutant protease gene introduced was determined based on halo formation status. The transformant was inoculated into 5 mL of a seed medium [6.0% (w/v) polypeptone S, 0.05% yeast extract, 1.0% maltose, 0.02% magnesium sulfate heptahydrate, 0.1% potassium dihydrogen phosphate, 0.25% sodium carbonate, and 30 ppm tetracycline], and was then subjected to a shaking culture at 30° C. for 16 hours. Subsequently, the seed culture medium (1% (v/v)) was inoculated into 20 mL of a main medium [8% polypeptone S, 0.3% yeast extract, 10% maltose, 0.04% magnesium sulfate heptahydrate, 0.2% potassium dihydrogen phosphate, 1.5% anhydrous sodium carbonate, and 30 ppm tetracycline], and was then subjected to a shaking culture at 30° C. for 3 days. The obtained culture medium was centrifuged to obtain a culture supernatant containing an alkaline protease mutant. The protein mass was measured using Protein Assay Rapid Kit Wako (Wako Pure Chemical Industries, Ltd.).

Example 2 Production of Alkaline Protease Multiple Mutants

With reference to the descriptions of JP-B-5202690, JP-A-2002-218989, JP-A-2002-306176, JP-A-2004-000122, JP-A-2004-305176, JP-A-2006-129865, JP-A-2007-061101, JP-A-2008-212084, JP-A-2010-273672, JP-A-2010-273673, and JP-A-2013-233141, a mutation was introduced into a wild-type KP43 protease (SEQ ID NO: 2) to produce the following KP43 protease mutants.

(1) Single Mutant (SEQ ID NO: 3):
Alanine at position 132 was substituted with threonine (JP-B-5202690), (2) 10-Fold mutant-1 (SEQ ID NO: 4):
Tyrosine at position 195 was substituted with glutamine (JP-A-2002-218989);
aspartic acid at position 369 was substituted with asparagine (JP-A-2002-306176);
threonine at position 65 was substituted with proline, valine at position 273 was substituted with isoleucine, threonine at position 359 was substituted with serine, and serine at position 387 was substituted with alanine (JP-A-2004-000122);
asparagine at position 166 was substituted with glycine, and glycine at position 167 was substituted with valine (JP-A-2004-305176); and serine at position 16 was substituted with valine, and asparagine at position 83 was substituted with alanine (JP-A-2010-273672, and JP-A-2010-273673), (3) 11-Fold Mutant-1 (SEQ ID NO: 5):

Alanine at position 132 was substituted with threonine (JP-B-5202690);

Tyrosine at position 195 was substituted with glutamine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

asparagine at position 166 was substituted with glycine, and glycine at position 167 was substituted with valine (JP-A-2004-305176); and serine at position 16 was substituted with valine, and asparagine at position 83 was substituted with alanine (JP-A-2010-273672, and JP-A-2010-273673), (4) 11-Fold Mutant-2 (SEQ ID NO: 6):

Tyrosine at position 195 was substituted with glutamine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

asparagine at position 166 was substituted with glycine, and glycine at position 167 was substituted with valine (JP-A-2004-305176); and alanine at position 133 was substituted with serine, valine at position 134 was substituted with threonine, and serine was inserted between the position 133 and the position 134 (JP-A-2006-129865), (5) 16-Fold Mutant (SEQ ID NO: 7):

Tyrosine at position 195 was substituted with glutamine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

asparagine at position 166 was substituted with glycine, and glycine at position 167 was substituted with valine (JP-A-2004-305176);

alanine at position 133 was substituted with serine, valine at position 134 was substituted with threonine, and serine was inserted between the position 133 and the position 134 (JP-A-2006-129865); and serine at position 40 was substituted with isoleucine, threonine at position 59 was substituted with valine, serine at position 81 was substituted with leucine, serine at position 191 was substituted with leucine, and asparagine at position 405 was substituted with leucine (JP-A-2013-233141).

(6) 10-Fold Mutant-2 (SEQ ID NO: 8):

Alanine at position 132 was substituted with threonine (JP-B-5202690);

Tyrosine at position 195 was substituted with arginine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

asparagine at position 166 was substituted with glycine, and glycine at position 167 was substituted with valine (JP-A-2004-305176); and asparagine at position 83 was substituted with alanine (JP-A-2010-273672), (7) 11-Fold mutant-3 (SEQ ID NO: 9):

Tyrosine at position 195 was substituted with arginine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

asparagine at position 166 was substituted with glycine, and glycine at position 167 was substituted with valine (JP-A-2004-305176); and alanine at position 133 was substituted with serine, valine at position 134 was substituted with threonine, and serine was inserted between the position 133 and the position 134 (JP-A-2006-129865), (8) 12-Fold mutant (SEQ ID NO: 10):

Tyrosine at position 195 was substituted with glutamine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

asparagine at position 166 was substituted with glycine, and glycine at position 167 was substituted with valine (JP-A-2004-305176);

asparagine at position 83 was substituted with alanine, and alanine at position 319 was substituted with valine (JP-A-2010-273672), and serine at position 16 was substituted with valine, and glutamine at position 204 was substituted with aspartic acid (JP-A-2010-273673), (9) 14-Fold Mutant (SEQ ID NO: 11):

Tyrosine at position 195 was substituted with arginine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

asparagine at position 166 was substituted with glycine, and glycine at position 167 was substituted with valine (JP-A-2004-305176);

alanine at position 133 was substituted with serine, valine at position 134 was substituted with threonine, and serine was inserted between the position 133 and the position 134 (JP-A-2006-129865), and serine at position 194 was substituted with arginine, lysine at position 212 was substituted with arginine, and glutamine at position 379 was substituted with arginine (JP-A-2008-212084).

The above-described single mutant (SEQ ID NO: 3), 10-fold mutant-1 (SEQ ID NO: 4), 11-fold mutant-1 (SEQ ID NO: 5), 11-fold mutant-2 (SEQ ID NO: 6), 16-fold mutant (SEQ ID NO: 7), 10-fold mutant-2 (SEQ ID NO: 8), 11-fold mutant-3 (SEQ ID NO: 9), 12-fold mutant (SEQ ID NO: 10), and 14-fold mutant (SEQ ID NO: 11) had 99.8%, 97.7%, 97.5%, 97.5%, 96.3%, 97.7%, 97.5%, 97.2%, and 96.8% of an identity of the amino acid sequence, respectively, to the wild-type KP43 protease (SEQ ID NO: 2).

Into a polynucleotide encoding each of the above obtained mutants, such a mutation was introduced that the alanine at a position corresponding to position 294 of SEQ ID NO: 2 was substituted with threonine (A294T with respect to SEQ ID NOS: 3 to 5, 8, and 10, and A295T with respect to SEQ ID NOS: 6, 7, 9, and 11) according to the same procedures as those of Example 1. Thereafter, host was transformed with each mutant, and the obtained transformant was then cultured to obtain a culture supernatant containing an alkaline protease mutant. The protein mass thereof was then measured. In the following Examples, alkaline protease mutants obtained in Examples 1 and 2, which have T at a position corresponding to position 294 of SEQ ID NO: 2, are collectively referred to as an "A294T mutant."

Example 3 Evaluation of Stability of Alkaline Protease Mutant in Chelating Agent-Containing Solution (1) Evaluation of Stability in Citrate Aqueous Solution The culture supernatant of the A294T mutant obtained in Example 1 was added to a 20 mM Tris-HCl buffer (pH8.0), which contained or did not contain 2 mM 3Na citrate, and the mixture was then fully blended to obtain an enzyme solution (final concentration of enzyme: 0.017 mg/mL). The enzyme solution was fractionated in an amount of 200 µL each into a 96-well assay plate, and 10 µL of 10 mM Glt-Ala-Ala-Pro-Leu-pNA.H$_2$O (PEPTIDE INSTITUTE, INC.) was then added thereto. Thereafter, the absorbance at 405 nm was measured over time, using a microplate reader (Infinite M200Pro; TECAN), while shaking at 30° C. for 15 minutes. The absorbance-changing rate (mOD 405/min) was considered to be enzyme activity, and the initial activity value was obtained. The residual activity value of the enzyme solution, which had been heated at 70° C. for 10 minutes, was obtained by the same method as that for the measurement of the initial activity value. According to the following equation, the residual activity (%) of alkaline protease was calculated:

Residual activity (%)=Residual activity value/Initial activity value×100

Subsequently, the relative value of the residual activity (residual relative activity (%)) of the A294T mutant was obtained, when the residual activity of the parent alkaline protease (wild-type KP43 protease; SEQ ID NO: 2) was set at 100%.

Likewise, with regard to the single mutant (SEQ ID NO: 3), 11-fold mutant-2 (SEQ ID NO: 6), 14-fold mutant (SEQ ID NO: 11) and 16-fold mutant (SEQ ID NO: 7), which had been obtained in Example 2, the residual activity (%) of the A294T mutant was calculated, and the residual relative activity (%) of each mutant to the parent alkaline protease was then obtained.

(2) Evaluation of Stability in EDTA Aqueous Solution

The culture supernatant of the A294T mutant obtained in Example 1 was added to a 20 mM Tris-HCl buffer (pH8.0), which contained or did not contain 1 mM EDTA, and the mixture was then fully blended to obtain an enzyme solution (final concentration of enzyme: 0.017 mg/mL). Using this enzyme solution, the residual activity (%) of the alkaline protease was calculated under the same conditions as those in the above (1), and the residual relative activity (%) of the mutant to the parent alkaline protease was then obtained.

Likewise, with regard to the single mutant (SEQ ID NO: 3), 10-fold mutant-1 (SEQ ID NO: 4), 10-fold mutant-2 (SEQ ID NO: 8), 11-fold mutant-1 (SEQ ID NO: 5), 11-fold mutant-2 (SEQ ID NO: 6), 11-fold mutant-3 (SEQ ID NO: 9), 12-fold mutant (SEQ ID NO: 10) and 16-fold mutant (SEQ ID NO: 7), which had been obtained in Example 2, the residual activity (%) of the A294T mutant was calculated, and the residual relative activity (%) of each mutant to the parent alkaline protease was then obtained.

(3) Results

The residual relative activities of the A294T mutants in the citrate aqueous solution, which were measured in the above (1), are shown in FIG. 1 and Table 2. The residual relative activities of the A294T mutants in the EDTA aqueous solution, which were measured in the above (2), are shown in FIGS. 2 and 3 and Tables 3 and 4. The remaining activities of the A294T mutants were equivalent in comparison to their parent alkaline protease in a solution not containing a chelating agent, but the A294T mutants had higher residual activities in a chelating agent-containing solution. These results show that the stability of the A294T mutant in a chelating agent-containing solution has been improved, in comparison to that of the parent alkaline protease thereof.

TABLE 2

| | Residual relative activity (%) | |
| --- | --- | --- |
| | Without 3Na citrate | With 2 mM 3Na citrate |
| Wild type | 100.0 | 100.0 |
| A294T | 110.3 | 311.1 |
| Single mutant | 100.0 | 100.0 |
| Single mutant/A294T | 110.5 | 204.8 |
| 11-fold mutant-2 | 100.0 | 100.0 |
| 11-fold mutant-2/A294T | 109.0 | 184.5 |
| 14-fold mutant | 100.0 | 100.0 |
| 14-fold mutant/A294T | 86.2 | 144.7 |
| 16-fold mutant | 100.0 | 100.0 |
| 16-fold mutant/A294T | 118.5 | 393.5 |

TABLE 3

| | Residual relative activity (%) | |
| --- | --- | --- |
| | Without EDTA | With 1 mM EDTA |
| Wild type | 100.0 | 100.0 |
| A294T | 98.1 | 199.5 |
| Single mutant | 100.0 | 100.0 |
| Single mutant/A294T | 99.5 | 324.9 |
| 10-fold mutant-1 | 100.0 | 100.0 |
| 10-fold mutant-1/A294T | 101.6 | 473.0 |
| 10-fold mutant-2 | 100.0 | 100.0 |
| 10-fold mutant-2/A294T | 99.4 | 1304.2 |
| 11-fold mutant-1 | 100.0 | 100.0 |
| 11-fold mutant 1/A294T | 93.7 | 598.3 |
| 11-fold mutant-2 | 100.0 | 100.0 |
| 11-fold mutant-2/A294T | 101.6 | 545.4 |

TABLE 4

| | Residual relative activity (%) | |
|---|---|---|
| | Without EDTA | With 1 mM EDTA |
| 11-fold mutant-3 | 100.0 | 100.0 |
| 11-fold mutant-3/A294T | 143.3 | 549.6 |
| 12-fold mutant | 100.0 | 100.0 |
| 12-fold mutant/A294T | 104.1 | 309.9 |
| 16-fold mutant | 100.0 | 100.0 |
| 16-fold mutant/A294T | 98.9 | 532.7 |

Example 4 Evaluation of Stability of Alkaline Protease Mutant in Detergent Composition A commercially available liquid detergent composition for clothes (Ultra Attack Neo; Kao Corporation, released in 2015, citrate mixed) was heated in a microwave oven to deactivate the enzyme contained in the product. To this product, the A294T mutant of Example 1 or wild-type KP43 protease was added in an amount of 1.0% (v/v), and the obtained mixture was then fully blended to obtain an enzyme-containing detergent composition. The detergent composition was 10-fold diluted with ion exchange water, and the diluted solution was then fully stirred. The thus obtained detergent solution was fractionated in an amount of 200 µL each into a 96-well assay plate, and 10 µL of 10 mM Glt-Ala-Ala-Pro-Leu-pNA.H$_2$O (PEPTIDE INSTITUTE, INC.) was then added thereto. Thereafter, the absorbance at 405 nm was measured over time, using a microplate reader (Infinite M200Pro; TECAN), while shaking at 30° C. for 15 minutes. The absorbance-changing rate (mOD 405/min) was considered to be enzyme activity, and the initial activity value was obtained. Moreover, after the detergent composition was preserved at 40° C. for 28 days, the residual activity value was obtained by the same method as that for the measurement of the initial activity value. According to the following equation, the residual activity (%) of alkaline protease was calculated:

Residual activity (%)=Residual activity value/Initial activity value×100

Subsequently, the residual relative activity (%) of the A294T mutant was obtained, when the residual activity of the wild-type KP43 protease was set at 100%.

The results are shown in Table 5. In comparison to the wild-type KP43 protease, which was the parent alkaline protease of the A294T mutant, the preservation stability of the A294T mutant was approximately 2 times improved in the detergent composition.

TABLE 5

| Enzyme | Residual relative activity (%) after preservation at 40° C. for 28 days |
|---|---|
| Wild type | 100.0 |
| A294T | 198.0 |

Reference Example 1

The single mutant and multiple mutants of KP43 protease, which was used as the parent alkaline protease in Example 2, were examined, in terms of citric acid resistance and EDTA resistance, under the same conditions as those in Examples 3 and 4. The results regarding citric acid resistance are shown in Table 6, and the results regarding EDTA resistance are shown in Table 7. The values shown in Tables 6 and 7 each indicate the residual relative activity (%) of each mutant, when the residual activity of wild-type KP43 protease (SEQ ID NO: 2) is set at 100%. Each parent alkaline protease had equivalent or higher resistance to chelating agents, in comparison to the wild-type KP43 protease. These results show that the chelating agent resistance of the A294T mutants shown in Examples 3 and 4 is superior to that of any of the parent alkaline protease and the wild-type protease.

TABLE 6

| 2 mM 3Na citrate | |
|---|---|
| Enzyme | Residual relative activity (%) |
| Wild type | 100.0 |
| Single mutant | 115.9 |
| 14-fold mutant | 170.7 |
| 16-fold mutant | 165.0 |

TABLE 7

| 1 mM EDTA | |
|---|---|
| Enzyme | Residual relative activity (%) |
| Wild type | 100.0 |
| Single mutant | 113.3 |
| 10-fold mutant-1 | 108.3 |
| 10-fold mutant-2 | 137.3 |
| 11-fold mutant-1 | 126.5 |
| 11-fold mutant-2 | 120.4 |
| 16-fold mutant | 103.9 |

As given above, the embodiments according to the present invention are explained. However, it should be understood that these embodiments are not intended to limit the present invention to the explained specific embodiments. Various other modifications and corrections, which are within the scope of the present invention, are obvious to a person skilled in the art.

Publications and patent applications cited in the present description are incorporated herein by reference as if set forth herein in their entirety.

What is claimed is:

1. An alkaline protease mutant, the amino acid sequence of the mutant consisting of
   (a) the amino acid sequence of SEQ ID NO:2, or
   (b) an amino acid sequence having at least 97% homology to SEQ ID NO:2,
but in which, in the amino acid sequence of (a) and (b), the amino acid residue at position 294 in the amino acid sequence shown in SEQ ID NO:2, or at a position corresponding thereto, is a threonine.

2. The alkaline protease mutant according to claim 1, wherein the amino acid sequence has at least 97% homology to the sequence of SEQ ID NO:2 and has one or more amino acid residues selected from the group consisting of the following (a') to (ds'):

(a') the amino acid residue at position 6 of the amino acid sequence as shown in SEQ ID NO: 2 or at a position corresponding thereto, which is S, T, C, Q, Y, R, K, H, A, V, L, I, M, W or F;

(b') the amino acid residue at position 9 of the amino acid sequence as shown in SEQ ID NO: 2 or at a position corresponding thereto, which is Q;

(c') the amino acid residue at position 11 of the amino acid sequence as shown in SEQ ID NO: 2 or at a position corresponding thereto, which is G, S or N;

(d') the amino acid residue at position 15 of the amino acid sequence as shown in SEQ ID NO: 2 or at a position corresponding thereto, which is H, C, Q, D, E, R, A, V, M, W or F;

(e') the amino acid residue at position 16 of the amino acid sequence as shown in SEQ ID NO: 2 or at a position corresponding thereto, which is T, Q, V, C, Y, D, E, R, K, H, L, I, M, W or F;

(f') the amino acid residue at position 20 of the amino acid sequence as shown in SEQ ID NO: 2 or at a position corresponding thereto, which is F or A;

(g') the amino acid residue at position 22 of the amino acid sequence as shown in SEQ ID NO: 2 or at a position corresponding thereto, which is W;

(h') the amino acid residue at position 23 of the amino acid sequence as shown in SEQ ID NO: 2 or at a position corresponding thereto, which is N;

(i') the amino acid residue at position 37 of the amino acid sequence as shown in SEQ ID NO: 2 or at a position corresponding thereto, which is T;

(j') the amino acid residue at position 40 of the amino acid sequence as shown in SEQ ID NO: 2 or at a position corresponding thereto, which is V, L, I, W or F;

(k') the amino acid residue at position 41 of the amino acid sequence as shown in SEQ ID NO: 2 or at a position corresponding thereto, which is I;

(l') the amino acid residue at position 46 of the amino acid sequence as shown in SEQ ID NO: 2 or at a position corresponding thereto, which is S, T, C, N, Q, Y, E, K, H, A, V, L, I, M or W;

(m') the amino acid residue at position 49 of the amino acid sequence as shown in SEQ ID NO: 2 or at a position corresponding thereto, which is Q;

(n') the amino acid residue at position 52 of the amino acid sequence as shown in SEQ ID NO: 2 or at a position corresponding thereto, which is G or S;

(o') the amino acid residue at position 53 of the amino acid sequence as shown in SEQ ID NO: 2 or at a position corresponding thereto, which is A, V or I;

(p') the amino acid residue at position 54 of the amino acid sequence as shown in SEQ ID NO: 2 or at a position corresponding thereto, which is G, S, T, C, N, Q, D, E, R, H, A, V, M, W, F or P;

(q') the amino acid residue at position 56 of the amino acid sequence as shown in SEQ ID NO: 2 or at a position corresponding thereto, which is V;

(r') the amino acid residue at position 57 of the amino acid sequence as shown in SEQ ID NO: 2 or at a position corresponding thereto, which is S, T, C, Q, D, E, R, K, H, A, V, L, I, M, W, F or P;

(s') the amino acid residue at position 59 of the amino acid sequence as shown in SEQ ID NO: 2 or at a position corresponding thereto, which is V, L, I, M, W or F;

(t') the amino acid residue at position 60 of the amino acid sequence as shown in SEQ ID NO: 2 or at a position corresponding thereto, which is V, L, I, W or F;

(u') the amino acid residue at position 63 of the amino acid sequence as shown in SEQ ID NO: 2 or at a position corresponding thereto, which is S, D or L;

(v') the amino acid residue at position 65 of the amino acid sequence as shown in SEQ ID NO: 2 or at a position corresponding thereto, which is W or P;

(w') the amino acid residue at position 66 of the amino acid sequence as shown in SEQ ID NO: 2 or at a position corresponding thereto, which is G, S, T, C, Q, D, E, H, A, V, L, I, M or W;

(x') the amino acid residue at position 80 of the amino acid sequence as shown in SEQ ID NO: 2 or at a position corresponding thereto, which is H or A;

(y') the amino acid residue at position 81 of the amino acid sequence as shown in SEQ ID NO: 2 or at a position corresponding thereto, which is Q, Y, L, I, W or F;

(z') the amino acid residue at position 82 of the amino acid sequence as shown in SEQ ID NO: 2 or at a position corresponding thereto, which is G, S, C, Q, D, E, R, K, H, A or M;

(aa') the amino acid residue at position 83 of the amino acid sequence as shown in SEQ ID NO: 2 or at a position corresponding thereto, which is S, C or A;

(ab') the amino acid residue at position 84 of the amino acid sequence as shown in SEQ ID NO: 2 or at a position corresponding thereto, which is R;

(ac') the amino acid residue at position 89 of the amino acid sequence as shown in SEQ ID NO: 2 or at a position corresponding thereto, which is H;

(ad') the amino acid residue at position 91 of the amino acid sequence as shown in SEQ ID NO: 2 or at a position corresponding thereto, which is C;

(ae') the amino acid residue at position 100 of the amino acid sequence as shown in SEQ ID NO: 2 or at a position corresponding thereto, which is L, I, W or F;

(af') the amino acid residue at position 101 of the amino acid sequence as shown in SEQ ID NO: 2 or at a position corresponding thereto, which is S, T, C, N, Q, Y, D, E, R, K, H, A, V, L, I, M, W, F or P;

(ag') the amino acid residue at position 102 of the amino acid sequence as shown in SEQ ID NO: 2 or at a position corresponding thereto, which is S, T, C, Q, Y, D, E, R, K, H, A, V, L, I, M, W, F or P;

(ah') the amino acid residue at position 103 of the amino acid sequence as shown in SEQ ID NO: 2 or at a position corresponding thereto, which is S, T, C, Q, Y, D, E, R, K, H, A, V, L, I, M, W, F or P;

(ai') the amino acid residue at position 104 of the amino acid sequence as shown in SEQ ID NO: 2 or at a position corresponding thereto, which is S, T, C, Q, Y, D, E, R, K, H, A, V, L, I, M, W, F or P;

(aj') the amino acid residue at position 105 of the amino acid sequence as shown in SEQ ID NO: 2 or at a position corresponding thereto, which is S, T, C, Q, Y, D, E, R, K, H, A, V, L, I, M, W, F or P;

(ak') the amino acid residue at position 106 of the amino acid sequence as shown in SEQ ID NO: 2 or at a position corresponding thereto, which is S, T, C, Q, Y, D, E, R, K, H, A, V, L, I, M, W, F or P;

(al') the amino acid residue at position 107 of the amino acid sequence as shown in SEQ ID NO: 2 or at a position corresponding thereto, which is S, R, K or A;

(am') the amino acid residue at position 109 of the amino acid sequence as shown in SEQ ID NO: 2 or at a position corresponding thereto, which is L, I or F;

(an') the amino acid residue at position 113 of the amino acid sequence as shown in SEQ ID NO: 2 or at a position corresponding thereto, which is L or W;

(ao') the amino acid residue at position 119 of the amino acid sequence as shown in SEQ ID NO: 2 or at a position corresponding thereto, which is G, S, T, C, N, Q, D, E, R, K, H, A, V, M, W, F or P;

(ap') the amino acid residue at position 120 of the amino acid sequence as shown in SEQ ID NO: 2 or at a position corresponding thereto, which is Y, R, I, W or F;

(aq') the amino acid residue at position 124 of the amino acid sequence as shown in SEQ ID NO: 2 or at a position corresponding thereto, which is K or A;

(ar') the amino acid residue at position 132 of the amino acid sequence as shown in SEQ ID NO: 2 or at a position corresponding thereto, which is S, T, N, Q, D, I or M;

(as') the amino acid residue at position 133 of the amino acid sequence as shown in SEQ ID NO: 2 or at a position corresponding thereto, which is G, S, T, C, N, Q, D, E, R, K, H, V, L, I, M, W, F or P;

(at') the amino acid residue at position 134 of the amino acid sequence as shown in SEQ ID NO: 2 or at a position corresponding thereto, which is G, S, T or A;

(au') the amino acid residue between position 133 of the amino acid sequence as shown in SEQ ID NO: 2 or a position corresponding thereto, and position 134 thereof or a position corresponding thereto, which is G, S, T, N, Q, Y, R, K, H, A, L, I, M or W;

(av') the amino acid residue at position 135 of the amino acid sequence as shown in SEQ ID NO: 2 or at a position corresponding thereto, which is R, A, L or M;

(aw') the amino acid residue at position 136 of the amino acid sequence as shown in SEQ ID NO: 2 or at a position corresponding thereto, which is S, T, C, Q, Y, D, E, R, K, H, A, V, L, I, M, W, F or P;

(ax') the amino acid residue at position 138 of the amino acid sequence as shown in SEQ ID NO: 2 or at a position corresponding thereto, which is G, S, C, N, Q, D, E, R, K, H, A, V, M, W, F or P;

(ay') the amino acid residue at position 140 of the amino acid sequence as shown in SEQ ID NO: 2 or at a position corresponding thereto, which is L, W or F;

(az') the amino acid residue at position 148 of the amino acid sequence as shown in SEQ ID NO: 2 or at a position corresponding thereto, which is G, S, T, C, N, Q, D, E, R, K, H, A, M, W, F or P;

(ba') the amino acid residue at position 151 of the amino acid sequence as shown in SEQ ID NO: 2 or at a position corresponding thereto, which is F;

(bb') the amino acid residue at position 163 of the amino acid sequence as shown in SEQ ID NO: 2 or at a position corresponding thereto, which is S, T, N, Q, D, K, H, V, L, I or F;

(bc') the amino acid residue at position 166 of the amino acid sequence as shown in SEQ ID NO: 2 or at a position corresponding thereto, which is G, V, L, I, W or F;

(bd') the amino acid residue at position 167 of the amino acid sequence as shown in SEQ ID NO: 2 or at a position corresponding thereto, which is V;

(be') the amino acid residue at position 170 of the amino acid sequence as shown in SEQ ID NO: 2 or at a position corresponding thereto, which is V or L;

(bf') the amino acid residue at position 171 of the amino acid sequence as shown in SEQ ID NO: 2 or at a position corresponding thereto, which is G, T, E or A;

(bg') the amino acid residue at position 187 of the amino acid sequence as shown in SEQ ID NO: 2 or at a position corresponding thereto, which is S;

(bh') the amino acid residue at position 191 of the amino acid sequence as shown in SEQ ID NO: 2 or at a position corresponding thereto, which is V, L, I, W or F;

(bi') the amino acid residue at position 193 of the amino acid sequence as shown in SEQ ID NO: 2 or at a position corresponding thereto, which is S, T, C, Q, Y, D, E, R, K, H, A, V, L, I, M, W, F or P;

(bj') the amino acid residue at position 194 of the amino acid sequence as shown in SEQ ID NO: 2 or at a position corresponding thereto, which is Y, R or K;

(bk') the amino acid residue at position 195 of the amino acid sequence as shown in SEQ ID NO: 2 or at a position corresponding thereto, which is G, S, T, C, N, Q, D, E, R, K, H, A, V, L, I, M, W, F or P;

(bl') the amino acid residue at position 200 of the amino acid sequence as shown in SEQ ID NO: 2 or at a position corresponding thereto, which is W;

(bm') the amino acid residue at position 204 of the amino acid sequence as shown in SEQ ID NO: 2 or at a position corresponding thereto, which is S, T, C, N, D, E, R, K, H, V, L, I, M, W or P;

(bn') the amino acid residue at position 205 of the amino acid sequence as shown in SEQ ID NO: 2 or at a position corresponding thereto, which is S, T, C, N, Q, Y, E, K, H, A, V, L, I, M or W;

(bo') the amino acid residue at position 212 of the amino acid sequence as shown in SEQ ID NO: 2 or at a position corresponding thereto, which is N, Q, R, V, L or W;

(bp') the amino acid residue at position 226 of the amino acid sequence as shown in SEQ ID NO: 2 or at a position corresponding thereto, which is Y;

(bq') the amino acid residue at position 233 of the amino acid sequence as shown in SEQ ID NO: 2 or at a position corresponding thereto, which is L, I or W;

(br') the amino acid residue at position 237 of the amino acid sequence as shown in SEQ ID NO: 2 or at a position corresponding thereto, which is N;

(bs') the amino acid residue at position 238 of the amino acid sequence as shown in SEQ ID NO: 2 or at a position corresponding thereto, which is L;

(bt') the amino acid residue at position 243 of the amino acid sequence as shown in SEQ ID NO: 2 or at a position corresponding thereto, which is Y, L or I;

(bu') the amino acid residue at position 245 of the amino acid sequence as shown in SEQ ID NO: 2 or at a position corresponding thereto, which is N;

(bv') the amino acid residue at position 246 of the amino acid sequence as shown in SEQ ID NO: 2 or at a position corresponding thereto, which is Y, V, L, W or F;

(bw') the amino acid residue at position 247 of the amino acid sequence as shown in SEQ ID NO: 2 or at a position corresponding thereto, which is S, T, C, N, Q, E, H, A, V, L, I, M, W or F;

(bx') the amino acid residue at position 248 of the amino acid sequence as shown in SEQ ID NO: 2 or at a position corresponding thereto, which is F;

(by') the amino acid residue at position 250 of the amino acid sequence as shown in SEQ ID NO: 2 or at a position corresponding thereto, which is F;

(bz') the amino acid residue at position 251 of the amino acid sequence as shown in SEQ ID NO: 2 or at a position corresponding thereto, which is G, T, N, Q, D, A, V, L or I;

(ca') the amino acid residue at position 256 of the amino acid sequence as shown in SEQ ID NO: 2 or at a position corresponding thereto, which is S, T, C, Q, Y, D, E, R, K, H, A, V, L, I, W, F or P;

(cb') the amino acid residue at position 257 of the amino acid sequence as shown in SEQ ID NO: 2 or at a position corresponding thereto, which is V or I;

(cc') the amino acid residue at position 264 of the amino acid sequence as shown in SEQ ID NO: 2 or at a position corresponding thereto, which is G, S, T, C, Q, D, E, A, V, L, I or M;
(cd') the amino acid residue at position 273 of the amino acid sequence as shown in SEQ ID NO: 2 or at a position corresponding thereto, which is G, T or I;
(ce') the amino acid residue at position 275 of the amino acid sequence as shown in SEQ ID NO: 2 or at a position corresponding thereto, which is L, W or F;
(cf') the amino acid residue at position 277 of the amino acid sequence as shown in SEQ ID NO: 2 or at a position corresponding thereto, which is V, L, I or F;
(cg') the amino acid residue at position 281 of the amino acid sequence as shown in SEQ ID NO: 2 or at a position corresponding thereto, which is R;
(ch') the amino acid residue at position 296 of the amino acid sequence as shown in SEQ ID NO: 2 or at a position corresponding thereto, which is V;
(ci') the amino acid residue at position 297 of the amino acid sequence as shown in SEQ ID NO: 2 or at a position corresponding thereto, which is L, W or F;
(cj') the amino acid residue at position 304 of the amino acid sequence as shown in SEQ ID NO: 2 or at a position corresponding thereto, which is S;
(ck') the amino acid residue at position 313 of the amino acid sequence as shown in SEQ ID NO: 2 or at a position corresponding thereto, which is N;
(cl') the amino acid residue at position 319 of the amino acid sequence as shown in SEQ ID NO: 2 or at a position corresponding thereto, which is S, T, C, N, Q, Y, D, E, R, K, H, V, L, I, M, W, F or P;
(cm') the amino acid residue at position 320 of the amino acid sequence as shown in SEQ ID NO: 2 or at a position corresponding thereto, which is G, T, V, L, I or F;
(cn') the amino acid residue at position 326 of the amino acid sequence as shown in SEQ ID NO: 2 or at a position corresponding thereto, which is W;
(co') the amino acid residue at position 330 of the amino acid sequence as shown in SEQ ID NO: 2 or at a position corresponding thereto, which is M, W or F;
(cp') the amino acid residue at position 332 of the amino acid sequence as shown in SEQ ID NO: 2 or at a position corresponding thereto, which is G, T or V;
(cq') the amino acid residue at position 334 of the amino acid sequence as shown in SEQ ID NO: 2 or at a position corresponding thereto, which is L;
(cr') the amino acid residue at position 335 of the amino acid sequence as shown in SEQ ID NO: 2 or at a position corresponding thereto, which is F;
(cs') the amino acid residue at position 337 of the amino acid sequence as shown in SEQ ID NO: 2 or at a position corresponding thereto, which is G, S, T, C, Q, R, K, H, A or V;
(ct') the amino acid residue at position 342 of the amino acid sequence as shown in SEQ ID NO: 2 or at a position corresponding thereto, which is S, T, C, Q, Y, D, E, R, K, H, A, V, L, I, M, W, F or P;
(cu') the amino acid residue at position 343 of the amino acid sequence as shown in SEQ ID NO: 2 or at a position corresponding thereto, which is T;
(cv') the amino acid residue at position 346 of the amino acid sequence as shown in SEQ ID NO: 2 or at a position corresponding thereto, which is R;
(cw') the amino acid residue at position 357 of the amino acid sequence as shown in SEQ ID NO: 2 or at a position corresponding thereto, which is L;
(cx') the amino acid residue at position 359 of the amino acid sequence as shown in SEQ ID NO: 2 or at a position corresponding thereto, which is G, S, Q, V, L, I or F;
(cy') the amino acid residue at position 361 of the amino acid sequence as shown in SEQ ID NO: 2 or at a position corresponding thereto, which is V, I or W;
(cz') the amino acid residue at position 369 of the amino acid sequence as shown in SEQ ID NO: 2 or at a position corresponding thereto, which is N;
(da') the amino acid residue at position 376 of the amino acid sequence as shown in SEQ ID NO: 2 or at a position corresponding thereto, which is W;
(db') the amino acid residue at position 378 of the amino acid sequence as shown in SEQ ID NO: 2 or at a position corresponding thereto, which is L or W;
(dc') the amino acid residue at position 379 of the amino acid sequence as shown in SEQ ID NO: 2 or at a position corresponding thereto, which is D, E, R or K;
(dd') the amino acid residue at position 380 of the amino acid sequence as shown in SEQ ID NO: 2 or at a position corresponding thereto, which is F;
(de') the amino acid residue at position 385 of the amino acid sequence as shown in SEQ ID NO: 2 or at a position corresponding thereto, which is Y, M or P;
(df') the amino acid residue at position 386 of the amino acid sequence as shown in SEQ ID NO: 2 or at a position corresponding thereto, which is A, L, I or M;
(dg') the amino acid residue at position 387 of the amino acid sequence as shown in SEQ ID NO: 2 or at a position corresponding thereto, which is G, Q, E, R, K, H, A, V, L, I, M, W or F;
(dh') the amino acid residue at position 390 of the amino acid sequence as shown in SEQ ID NO: 2 or at a position corresponding thereto, which is G, S, T, Y or F;
(di') the amino acid residue at position 393 of the amino acid sequence as shown in SEQ ID NO: 2 or at a position corresponding thereto, which is Q;
(dj') the amino acid residue at position 396 of the amino acid sequence as shown in SEQ ID NO: 2 or at a position corresponding thereto, which is G;
(dk') the amino acid residue at position 403 of the amino acid sequence as shown in SEQ ID NO: 2 or at a position corresponding thereto, which is T or K;
(dl') the amino acid residue at position 405 of the amino acid sequence as shown in SEQ ID NO: 2 or at a position corresponding thereto, which is D, V, L, I, W, F or P;
(dm') the amino acid residue at position 406 of the amino acid sequence as shown in SEQ ID NO: 2 or at a position corresponding thereto, which is V, W or F;
(dn') the amino acid residue at position 407 of the amino acid sequence as shown in SEQ ID NO: 2 or at a position corresponding thereto, which is G or C;
(do') the amino acid residue at position 408 of the amino acid sequence as shown in SEQ ID NO: 2 or at a position corresponding thereto, which is N, Y, I or W;
(dp') the amino acid residue at position 409 of the amino acid sequence as shown in SEQ ID NO: 2 or at a position corresponding thereto, which is Y or W;
(dq') the amino acid residue at position 411 of the amino acid sequence as shown in SEQ ID NO: 2 or at a position corresponding thereto, which is A, V, L or P;

(dr') the amino acid residue at position 427 of the amino acid sequence as shown in SEQ ID NO: 2 or at a position corresponding thereto, which is R or V; and (ds') the amino acid residue at position 433 of the amino acid sequence as shown in SEQ ID NO: 2 or at a position corresponding thereto, which is L.

3. A polynucleotide encoding an alkaline protease mutant, the amino acid sequence of the mutant consisting of
   (a) the amino acid sequence of SEQ ID NO:2, or
   (b) an amino acid sequence having at least 97% homology to SEQ ID NO:2,
but in which, in the amino acid sequence of (a) and (b), the amino acid residue at position 294 in the amino acid sequence shown in SEQ ID NO:2, or at a position corresponding thereto, is a threonine.

4. A vector comprising the polynucleotide according to claim 3.

5. A transformant comprising the polynucleotide according to claim 3.

6. A method for producing an alkaline protease mutant comprising, culturing the transformant according to claim 5 and producing the alkaline protease mutant.

7. A detergent composition comprising the alkaline protease mutant according to claim 1.

8. A method for producing an alkaline protease mutant, comprising substituting the amino acid residue at a position corresponding to position 294 of the amino acid sequence as shown in SEQ ID NO: 2 with threonine, wherein the substituting is made to the amino acid sequence shown in SEQ ID NO: 2, or to an amino acid sequence having an identity of at least 97% to SEQ ID NO: 2.

9. A method for improving stability of alkaline protease to a chelating agent, comprising substituting the amino acid residue at a position corresponding to position 294 of the amino acid sequence as shown in SEQ ID NO: 2 with threonine, wherein the substituting is made to the amino acid sequence shown in SEQ ID NO: 2, or to an amino acid sequence having an identity of at least 97% to SEQ ID NO: 2.

10. The polynucleotide of claim 3, wherein the polynucleotide encodes an alkaline protease mutant, the mutant having an amino acid sequence that has at least 97% homology to the sequence of SEQ ID NO:2 and one or more amino acid residues selected from the group consisting of the following (a') to (ds'):
   (a') the amino acid residue at position 6 of the amino acid sequence as shown in SEQ ID NO: 2 or at a position corresponding thereto, which is S, T, C, Q, Y, R, K, H, A, V, L, I, M, W or F;
   (b') the amino acid residue at position 9 of the amino acid sequence as shown in SEQ ID NO: 2 or at a position corresponding thereto, which is Q,
   (c') the amino acid residue at position 11 of the amino acid sequence as shown in SEQ ID NO: 2 or at a position corresponding thereto, which is G, S or N;
   (d') the amino acid residue at position 15 of the amino acid sequence as shown in SEQ ID NO: 2 or at a position corresponding thereto, which is H, C, Q, D, E, R, A, V, M, W or F;
   (e') the amino acid residue at position 16 of the amino acid sequence as shown in SEQ ID NO: 2 or at a position corresponding thereto, which is T, Q, V, C, Y, D, E, R, K, H, L, L M, W or F;
   (f') the amino acid residue at position 20 of the amino acid sequence as shown in SEQ ID NO: 2 or at a position corresponding thereto, which is F or A;
   (g') the amino acid residue at position 22 of the amino acid sequence as shown in SEQ ID NO: 2 or at a position corresponding thereto, which is W;
   (h') the amino acid residue at position 23 of the amino acid sequence as shown in SEQ ID NO: 2 or at a position corresponding thereto, which is N;
   (i') the amino acid residue at position 37 of the amino acid sequence as shown in SEQ ID NO: 2 or at a position corresponding thereto, which is T;
   (j') the amino acid residue at position 40 of the amino acid sequence as shown in SEQ ID NO: 2 or at a position corresponding thereto, which is V, L, I, W or F;
   (k') the amino acid residue at position 41 of the amino acid sequence as shown in SEQ ID NO: 2 or at a position corresponding thereto, which is I;
   (l') the amino acid residue at position 46 of the amino acid sequence as shown in SEQ ID NO: 2 or at a position corresponding thereto, which is S, T, C, N, Q, Y, E, K, H, A, V, L, I, M or W;
   (m') the amino acid residue at position 49 of the amino acid sequence as shown in SEQ ID NO: 2 or at a position corresponding thereto, which is Q,
   (n') the amino acid residue at position 52 of the amino acid sequence as shown in SEQ ID NO: 2 or at a position corresponding thereto, which is G or S;
   (o') the amino acid residue at position 53 of the amino acid sequence as shown in SEQ ID NO: 2 or at a position corresponding thereto, which is A, V or I;
   (p') the amino acid residue at position 54 of the amino acid sequence as shown in SEQ ID NO: 2 or at a position corresponding thereto, which is G, S, T, C, N, Q, D, E, R, H, A, V, M, W, F or P;
   (q') the amino acid residue at position 56 of the amino acid sequence as shown in SEQ ID NO: 2 or at a position corresponding thereto, which is V;
   (r') the amino acid residue at position 57 of the amino acid sequence as shown in SEQ ID NO: 2 or at a position corresponding thereto, which is S, T, C, Q, D, E, R, K, H, A, V, L, I, M, W, F or P;
   (s') the amino acid residue at position 59 of the amino acid sequence as shown in SEQ ID NO: 2 or at a position corresponding thereto, which is V, L, I, M, W or F;
   (t') the amino acid residue at position 60 of the amino acid sequence as shown in SEQ ID NO: 2 or at a position corresponding thereto, which is V, L, I, W or F;
   (u') the amino acid residue at position 63 of the amino acid sequence as shown in SEQ ID NO: 2 or at a position corresponding thereto, which is S, D or L;
   (v') the amino acid residue at position 65 of the amino acid sequence as shown in SEQ ID NO: 2 or at a position corresponding thereto, which is W or P;
   (w') the amino acid residue at position 66 of the amino acid sequence as shown in SEQ ID NO: 2 or at a position corresponding thereto, which is G, S, T, C, Q, D, E, H, A, V, L, I, M or W;
   (x') the amino acid residue at position 80 of the amino acid sequence as shown in SEQ ID NO: 2 or at a position corresponding thereto, which is H or A;
   (y') the amino acid residue at position 81 of the amino acid sequence as shown in SEQ ID NO: 2 or at a position corresponding thereto, which is Q, Y, L, I, W or F;
   (z') the amino acid residue at position 82 of the amino acid sequence as shown in SEQ ID NO: 2 or at a position corresponding thereto, which is G, S, C, Q, D, E, R, K, H, A or M;

(aa') the amino acid residue at position 83 of the amino acid sequence as shown in SEQ ID NO: 2 or at a position corresponding thereto, which is S, C or A;

(ab') the amino acid residue at position 84 of the amino acid sequence as shown in SEQ ID NO: 2 or at a position corresponding thereto, which is R;

(ac') the amino acid residue at position 89 of the amino acid sequence as shown in SEQ ID NO: 2 or at a position corresponding thereto, which is H;

(ad') the amino acid residue at position 91 of the amino acid sequence as shown in SEQ ID NO: 2 or at a position corresponding thereto, which is C;

(ae') the amino acid residue at position 100 of the amino acid sequence as shown in SEQ ID NO: 2 or at a position corresponding thereto, which is L, I, W or F;

(af') the amino acid residue at position 101 of the amino acid sequence as shown in SEQ ID NO: 2 or at a position corresponding thereto, which is S, T, C, N, Q, Y, D, E, R, K, H, A, V, L, I, M, W, F or P;

(ag') the amino acid residue at position 102 of the amino acid sequence as shown in SEQ ID NO: 2 or at a position corresponding thereto, which is S, T, C, Q, Y, D, E, R, K, H, A, V, L, I, M, W, F or P;

(ah') the amino acid residue at position 103 of the amino acid sequence as shown in SEQ ID NO: 2 or at a position corresponding thereto, which is S, T, C, Q, Y, D, E, R, K, H, A, V, L, I, M, W, F or P;

(ai') the amino acid residue at position 104 of the amino acid sequence as shown in SEQ ID NO: 2 or at a position corresponding thereto, which is S, T, C, Q, Y, D, E, R, K, H, A, V, L, I, M, W, F or P;

(aj') the amino acid residue at position 105 of the amino acid sequence as shown in SEQ ID NO: 2 or at a position corresponding thereto, which is S, T, C, Q, Y, D, E, R, K, H, A, V, L, I, M, W, F or P;

(ak') the amino acid residue at position 106 of the amino acid sequence as shown in SEQ ID NO: 2 or at a position corresponding thereto, which is S, T, C, Q, Y, D, E, R, K, H, A, V, L, I, M, W, F or P;

(al') the amino acid residue at position 107 of the amino acid sequence as shown in SEQ ID NO: 2 or at a position corresponding thereto, which is S, R, K or A;

(am') the amino acid residue at position 109 of the amino acid sequence as shown in SEQ ID NO: 2 or at a position corresponding thereto, which is L, I or F;

(an') the amino acid residue at position 113 of the amino acid sequence as shown in SEQ ID NO: 2 or at a position corresponding thereto, which is L or W;

(ao') the amino acid residue at position 119 of the amino acid sequence as shown in SEQ ID NO: 2 or at a position corresponding thereto, which is G, S, T, C, N, Q, D, E, R, K, H, A, V, M, W, F or P;

(ap') the amino acid residue at position 120 of the amino acid sequence as shown in SEQ ID NO: 2 or at a position corresponding thereto, which is Y, R, I, W or F;

(aq') the amino acid residue at position 124 of the amino acid sequence as shown in SEQ ID NO: 2 or at a position corresponding thereto, which is K or A;

(ar') the amino acid residue at position 132 of the amino acid sequence as shown in SEQ ID NO: 2 or at a position corresponding thereto, which is S, T, N, Q, D, I or M;

(as') the amino acid residue at position 133 of the amino acid sequence as shown in SEQ ID NO: 2 or at a position corresponding thereto, which is G, S, T, C, N, Q, D, E, R, K, H, V, L, I, M, W, F or P;

(at') the amino acid residue at position 134 of the amino acid sequence as shown in SEQ ID NO: 2 or at a position corresponding thereto, which is G, S, T or A;

(au') the amino acid residue between position 133 of the amino acid sequence as shown in SEQ ID NO: 2 or a position corresponding thereto, and position 134 thereof or a position corresponding thereto, which is G, S, T, N, Q, Y, R, K, H, A, L, I, M or W;

(av') the amino acid residue at position 135 of the amino acid sequence as shown in SEQ ID NO: 2 or at a position corresponding thereto, which is R, A, L or M;

(aw') the amino acid residue at position 136 of the amino acid sequence as shown in SEQ ID NO: 2 or at a position corresponding thereto, which is S, T, C, Q, Y, D, E, R, K, H, A, V, L, I, M, W, F or P;

(ax') the amino acid residue at position 138 of the amino acid sequence as shown in SEQ ID NO: 2 or at a position corresponding thereto, which is G, S, C, N, Q, D, E, R, K, H, A, V, M, W, F or P;

(ay') the amino acid residue at position 140 of the amino acid sequence as shown in SEQ ID NO: 2 or at a position corresponding thereto, which is L, W or F;

(az') the amino acid residue at position 148 of the amino acid sequence as shown in SEQ ID NO: 2 or at a position corresponding thereto, which is G, S, T, C, N, Q, D, E, R, K, H, A, M, W, F or P;

(ba') the amino acid residue at position 151 of the amino acid sequence as shown in SEQ ID NO: 2 or at a position corresponding thereto, which is F;

(bb') the amino acid residue at position 163 of the amino acid sequence as shown in SEQ ID NO: 2 or at a position corresponding thereto, which is S, T, N, Q, D, K, H, V, L, I or F;

(bc') the amino acid residue at position 166 of the amino acid sequence as shown in SEQ ID NO: 2 or at a position corresponding thereto, which is G, V, L, I, W or F;

(bd') the amino acid residue at position 167 of the amino acid sequence as shown in SEQ ID NO: 2 or at a position corresponding thereto, which is V;

(be') the amino acid residue at position 170 of the amino acid sequence as shown in SEQ ID NO: 2 or at a position corresponding thereto, which is V or L;

(bf') the amino acid residue at position 171 of the amino acid sequence as shown in SEQ ID NO: 2 or at a position corresponding thereto, which is G, T, E or A;

(bg') the amino acid residue at position 187 of the amino acid sequence as shown in SEQ ID NO: 2 or at a position corresponding thereto, which is S;

(bh') the amino acid residue at position 191 of the amino acid sequence as shown in SEQ ID NO: 2 or at a position corresponding thereto, which is V, L, I, W or F;

(bi') the amino acid residue at position 193 of the amino acid sequence as shown in SEQ ID NO: 2 or at a position corresponding thereto, which is S, T, C, Q, Y, D, E, R, K, H, A, V, L, I, M, W, F or P;

(bj') the amino acid residue at position 194 of the amino acid sequence as shown in SEQ ID NO: 2 or at a position corresponding thereto, which is Y, R or K;

(bk') the amino acid residue at position 195 of the amino acid sequence as shown in SEQ ID NO: 2 or at a position corresponding thereto, which is G, S, T, C, N, Q, D, E, R, K, H, A, V, L, I, M, W, F or P;

(bl') the amino acid residue at position 200 of the amino acid sequence as shown in SEQ ID NO: 2 or at a position corresponding thereto, which is W;

(bm') the amino acid residue at position 204 of the amino acid sequence as shown in SEQ ID NO: 2 or at a position corresponding thereto, which is S, T, C, N, D, E, R, K, H, V, L, I, M, W or P;

(bn') the amino acid residue at position 205 of the amino acid sequence as shown in SEQ ID NO: 2 or at a position corresponding thereto, which is S, T, C, N, Q, Y, E, K, H, A, V, L, I, M or W;

(bo') the amino acid residue at position 212 of the amino acid sequence as shown in SEQ ID NO: 2 or at a position corresponding thereto, which is N, Q, R, V, L or W;

(bp') the amino acid residue at position 226 of the amino acid sequence as shown in SEQ ID NO: 2 or at a position corresponding thereto, which is Y;

(bq') the amino acid residue at position 233 of the amino acid sequence as shown in SEQ ID NO: 2 or at a position corresponding thereto, which is L, I or W;

(br') the amino acid residue at position 237 of the amino acid sequence as shown in SEQ ID NO: 2 or at a position corresponding thereto, which is N;

(bs') the amino acid residue at position 238 of the amino acid sequence as shown in SEQ ID NO: 2 or at a position corresponding thereto, which is L;

(bt') the amino acid residue at position 243 of the amino acid sequence as shown in SEQ ID NO: 2 or at a position corresponding thereto, which is Y, L or I;

(bu') the amino acid residue at position 245 of the amino acid sequence as shown in SEQ ID NO: 2 or at a position corresponding thereto, which is N;

(bv') the amino acid residue at position 246 of the amino acid sequence as shown in SEQ ID NO: 2 or at a position corresponding thereto, which is Y, V, L, W or F;

(bw') the amino acid residue at position 247 of the amino acid sequence as shown in SEQ ID NO: 2 or at a position corresponding thereto, which is S, T, C, N, Q, E, H, A, V, L, I, M, W or F;

(bx') the amino acid residue at position 248 of the amino acid sequence as shown in SEQ ID NO: 2 or at a position corresponding thereto, which is F;

(by') the amino acid residue at position 250 of the amino acid sequence as shown in SEQ ID NO: 2 or at a position corresponding thereto, which is F;

(bz') the amino acid residue at position 251 of the amino acid sequence as shown in SEQ ID NO: 2 or at a position corresponding thereto, which is G, T, N, Q, D, A, V, L or I;

(ca') the amino acid residue at position 256 of the amino acid sequence as shown in SEQ ID NO: 2 or at a position corresponding thereto, which is S, T, C, Q, Y, D, E, R, K, H, A, V, L, I, W, F or P;

(cb') the amino acid residue at position 257 of the amino acid sequence as shown in SEQ ID NO: 2 or at a position corresponding thereto, which is V or I;

(cc') the amino acid residue at position 264 of the amino acid sequence as shown in SEQ ID NO: 2 or at a position corresponding thereto, which is G, S, T, C, Q, D, E, A, V, L, I or M;

(cd') the amino acid residue at position 273 of the amino acid sequence as shown in SEQ ID NO: 2 or at a position corresponding thereto, which is G, T or I;

(ce') the amino acid residue at position 275 of the amino acid sequence as shown in SEQ ID NO: 2 or at a position corresponding thereto, which is L, W or F;

(cf') the amino acid residue at position 277 of the amino acid sequence as shown in SEQ ID NO: 2 or at a position corresponding thereto, which is V, L, I or F;

(cg') the amino acid residue at position 281 of the amino acid sequence as shown in SEQ ID NO: 2 or at a position corresponding thereto, which is R;

(ch') the amino acid residue at position 296 of the amino acid sequence as shown in SEQ ID NO: 2 or at a position corresponding thereto, which is V;

(ci') the amino acid residue at position 297 of the amino acid sequence as shown in SEQ ID NO: 2 or at a position corresponding thereto, which is L, W or F;

(cj') the amino acid residue at position 304 of the amino acid sequence as shown in SEQ ID NO: 2 or at a position corresponding thereto, which is S;

(ck') the amino acid residue at position 313 of the amino acid sequence as shown in SEQ ID NO: 2 or at a position corresponding thereto, which is N;

(cl') the amino acid residue at position 319 of the amino acid sequence as shown in SEQ ID NO: 2 or at a position corresponding thereto, which is S, T, C, N, Q, Y, D, E, R, K, H, V, L, I, M, W, F or P;

(cm') the amino acid residue at position 320 of the amino acid sequence as shown in SEQ ID NO: 2 or at a position corresponding thereto, which is G, T, V, L, I or F;

(cn') the amino acid residue at position 326 of the amino acid sequence as shown in SEQ ID NO: 2 or at a position corresponding thereto, which is W;

(co') the amino acid residue at position 330 of the amino acid sequence as shown in SEQ ID NO: 2 or at a position corresponding thereto, which is M, W or F;

(cp') the amino acid residue at position 332 of the amino acid sequence as shown in SEQ ID NO: 2 or at a position corresponding thereto, which is G, T or V;

(cq') the amino acid residue at position 334 of the amino acid sequence as shown in SEQ ID NO: 2 or at a position corresponding thereto, which is L;

(cr') the amino acid residue at position 335 of the amino acid sequence as shown in SEQ ID NO: 2 or at a position corresponding thereto, which is F;

(cs') the amino acid residue at position 337 of the amino acid sequence as shown in SEQ ID NO: 2 or at a position corresponding thereto, which is G, S, T, C, Q, R, K, H, A or V;

(ct') the amino acid residue at position 342 of the amino acid sequence as shown in SEQ ID NO: 2 or at a position corresponding thereto, which is S, T, C, Q, Y, D, E, R, K, H, A, V, L, I, M, W, F or P;

(cu') the amino acid residue at position 343 of the amino acid sequence as shown in SEQ ID NO: 2 or at a position corresponding thereto, which is T;

(cv') the amino acid residue at position 346 of the amino acid sequence as shown in SEQ ID NO: 2 or at a position corresponding thereto, which is R;

(cw') the amino acid residue at position 357 of the amino acid sequence as shown in SEQ ID NO: 2 or at a position corresponding thereto, which is L;

(cx') the amino acid residue at position 359 of the amino acid sequence as shown in SEQ ID NO: 2 or at a position corresponding thereto, which is G, S, Q, V, L, I or F;

(cy') the amino acid residue at position 361 of the amino acid sequence as shown in SEQ ID NO: 2 or at a position corresponding thereto, which is V, I or W;

(cz') the amino acid residue at position 369 of the amino acid sequence as shown in SEQ ID NO: 2 or at a position corresponding thereto, which is N;

(da') the amino acid residue at position 376 of the amino acid sequence as shown in SEQ ID NO: 2 or at a position corresponding thereto, which is W;

(db') the amino acid residue at position 378 of the amino acid sequence as shown in SEQ ID NO: 2 or at a position corresponding thereto, which is L or W;

(dc') the amino acid residue at position 379 of the amino acid sequence as shown in SEQ ID NO: 2 or at a position corresponding thereto, which is D, E, R or K;

(dd') the amino acid residue at position 380 of the amino acid sequence as shown in SEQ ID NO: 2 or at a position corresponding thereto, which is F;

(de') the amino acid residue at position 385 of the amino acid sequence as shown in SEQ ID NO: 2 or at a position corresponding thereto, which is Y, M or P;

(df') the amino acid residue at position 386 of the amino acid sequence as shown in SEQ ID NO: 2 or at a position corresponding thereto, which is A, L, I or M;

(dg') the amino acid residue at position 387 of the amino acid sequence as shown in SEQ ID NO: 2 or at a position corresponding thereto, which is G, Q, E, R, K, H, A, V, L, I, M, W or F;

(dh') the amino acid residue at position 390 of the amino acid sequence as shown in SEQ ID NO: 2 or at a position corresponding thereto, which is G, S, T, Y or F;

(di') the amino acid residue at position 393 of the amino acid sequence as shown in SEQ ID NO: 2 or at a position corresponding thereto, which is Q;

(dj') the amino acid residue at position 396 of the amino acid sequence as shown in SEQ ID NO: 2 or at a position corresponding thereto, which is G;

(dk') the amino acid residue at position 403 of the amino acid sequence as shown in SEQ ID NO: 2 or at a position corresponding thereto, which is T or K;

(dl') the amino acid residue at position 405 of the amino acid sequence as shown in SEQ ID NO: 2 or at a position corresponding thereto, which is D, V, L, I, W, F or P;

(dm') the amino acid residue at position 406 of the amino acid sequence as shown in SEQ ID NO: 2 or at a position corresponding thereto, which is V, W or F;

(dn') the amino acid residue at position 407 of the amino acid sequence as shown in SEQ ID NO: 2 or at a position corresponding thereto, which is G or C;

(do') the amino acid residue at position 408 of the amino acid sequence as shown in SEQ ID NO: 2 or at a position corresponding thereto, which is N, Y, I or W;

(dp') the amino acid residue at position 409 of the amino acid sequence as shown in SEQ ID NO: 2 or at a position corresponding thereto, which is Y or W;

(dq') the amino acid residue at position 411 of the amino acid sequence as shown in SEQ ID NO: 2 or at a position corresponding thereto, which is A, V, L or P;

(dr') the amino acid residue at position 427 of the amino acid sequence as shown in SEQ ID NO: 2 or at a position corresponding thereto, which is R or V; and (ds') the amino acid residue at position 433 of the amino acid sequence as shown in SEQ ID NO: 2 or at a position corresponding thereto, which is L.

11. A vector comprising the polynucleotide according to claim 10.

12. A transformant comprising the polynucleotide according to claim 10.

13. A method for producing an alkaline protease mutant comprising culturing the transformant according to claim 12 and producing the alkaline protease mutant.

14. A detergent composition comprising the alkaline protease mutant according to claim 2.

15. A transformant comprising the vector according to claim 4.

16. A method for producing an alkaline protease mutant comprising, culturing the transformant according to claim 15 and producing the alkaline protease mutant.

17. A transformant comprising the vector according to claim 11.

18. A method for producing an alkaline protease mutant comprising, culturing the transformant according to claim 17 and producing the alkaline protease mutant.

19. The alkaline protease mutant of claim 1, wherein the amino acid sequence of the mutant consists of (a) the amino acid sequence of SEQ ID NO:2, but in which, in the amino acid sequence of (a), the amino acid residue at position 294 in the amino acid sequence shown in SEQ ID NO:2, or at a position corresponding thereto, is a threonine.

20. The polynucleotide of claim 3, wherein the polynucleotide encodes an alkaline protease mutant, the amino acid sequence of the mutant consisting of (a) the amino acid sequence of SEQ ID NO:2, but in which, in the amino acid sequence of (a), the amino acid residue at position 294 in the amino acid sequence shown in SEQ ID NO:2, or at a position corresponding thereto, is a threonine.

* * * * *